(12) United States Patent
Iozzo

(10) Patent No.: US 6,524,573 B1
(45) Date of Patent: Feb. 25, 2003

(54) METHOD OF SUPPRESSING TUMOR CELL GROWTH BY ADMINISTERING A DECORIN GENE OR GENE PRODUCT

(75) Inventor: Renato V. Iozzo, Gladwyne, PA (US)

(73) Assignee: Thomas Jefferson University, Philadelphia, PA (US)

( * ) Notice: Subject to any disclaimer, the term of this patent is extended or adjusted under 35 U.S.C. 154(b) by 120 days.

(21) Appl. No.: 09/668,084

(22) Filed: Sep. 22, 2000

Related U.S. Application Data

(63) Continuation of application No. 09/222,377, filed on Dec. 29, 1999, now abandoned.
(60) Provisional application No. 60/071,727, filed on Dec. 20, 1997.

(51) Int. Cl.[7] .................. A01N 63/00; A61K 31/70; C12N 15/00; C12N 5/00
(52) U.S. Cl. .............. 424/93.2; 424/93.21; 435/320.1; 435/325; 435/455; 514/44
(58) Field of Search .................. 514/44; 435/69.1, 435/320.1, 325, 455; 424/93.2, 93.21

(56) References Cited

U.S. PATENT DOCUMENTS 5,824,655 A    10/1998    Border .................. 514/44

OTHER PUBLICATIONS

Anderson, Human gene therapy, 1998, Nature, vol. 392, pp. 25–30.*
Gomez–Navarro et al., Gene therapy for cancer, 1999, European Journal of Cancer, vol. 35, pp. 867–885.*
Mastrangelo et al., Gene therapy for human cancer: An essay for clinicians, 1996, Seminars in Oncology, vol. 23, pp. 4–21.*
Rosenberg et al., Gene therapist, heal thyself, 2000, Science, vol. 287, p. 1751.*
Verma, Gene theray: Beyond 2000, 2000, Molecular Therapy, vol. 1, p. 493.*
Varmus, Gene therapy: Not ready for prime time, 1996, Nature Medicine, vol. 2, pp. 7–8.*
Friedmann, Principles for human gene tharapy studies, 2000, Science, vol. 287, pp. 2163–2164.*
Verma et al., Gene therapy–promises, problems and prospects, 1997, Nature, vol. 389, pp. 239–242.*
Kelloff et al., Cancer chemoprevention: progress and promise, 1999, European Journal of Cancer, vol. 35, pp. 2031–2038.*
Santra et al., An Anti–oncogenic role for decorin, 2000, The Journal of Biological Chemistry, pp. 3515365161.*

Csordas et al., Sustained down–regulation of the epidermal growth factor receptor by decorin, 2000, The Journal of Biological Chemistry, pp. 32879–32887.*
Santra et al., Ectopic Expression of Decorin Protein Core Causes a Generalized Growth Suppression in Neoplastic Cells of Various Hostogenetic Origin and Requires Endogenous p21, an Inhibitor of Cyclin–dependent Kinases, J. Clin. Invest, vol. 100, No. 1, Jul. 1997, pp. 149–157.
Santra et al., De novo decorin gene expression suppresses the malignant phenotype in human colon cancer cells, Proc. Natl. Acad. Sci. USA, vol. 92, pp. 7016–7020, Jul. 1995 Biochemistry.
Ständer et al., Decorin gene transfer–mediated suppression of TGF–β synthesis abrogates experimental malignant glioma growth in vivo, Gene Therapy (1998) 5, pp. 1187–1194.
Moscatello et al., Decorin Suppresses Tumor Cell Growth by Activating the Epidermal Growth Factor Receptor, J. Clin. Invest., vol. 101, No. 2, Jan. 1998, pp. 406–412.
De Luca et al., Decorin–induced Growth Suppression Is Associated with Up–regulation of p21, an Inhibitor of Cyclin–dependent Kinases, J. Bio. Chem., vol. 271, No. 31, pp. 18961–18965, 1996.
Renato V. Iozzo, The Family of the Small Leucine–Rich Proteoglycans: Key Regulators of Matrix Assembly and Cellular Growth, Crit. Rev. Biochem. Molec. Bio., 32(2) :141–174 (1997).
Patel et al., Decorin Activates the Epidermal Growth Factor Receptor and Elevates Cytosolic Ca 2+ in A431 Carcinoma Cells, J. Bio. Chem., vol. 273, No. 6, pp. 3121–3124, 1998.
Database PubMed Medline, PMID 7797556, UI 95318142, Stover et al., Sre phosphorylation of the epidermal growth factor receptor at novel sites mediates receptor interaction with Sre and P85 alpha', abstract, *J. Biol. Chem.*, 270 (6) :15591–15597, see abstract, lines 11–14 (Jun. 1995).
Isaka et al., "Gene therapy by skeletal muscle expression of decorin prevents fibrotic disease in rat kidney", *Nature Medicine*, Apr. 1996, vol. 2, No. 4 pp. 418–423.
De Luca et al., "Decorin–induced growth suppression is associated with up–regulation of p21, an inhibitor of cyclin–dependent kinases", *Journal of Biological Chemistry*, Aug. 2, 1996, vol. 271, No. 31, pp. 18961–18965.

* cited by examiner

*Primary Examiner*—Scott D. Priebe
*Assistant Examiner*—Sumesh Kaushal
(74) *Attorney, Agent, or Firm*—Janet B. Smith

(57) ABSTRACT

A method of suppressing tumor growth is provided wherein decorin gene or its gene products are administered so that epidermal growth factor receptor activity is induced. This specific mechanism has been linked to tumor growth suppression.

10 Claims, 9 Drawing Sheets

METHOD OF SUPPRESSING TUMOR CELL GROWTH BY ADMINISTERING A DECORIN GENE OR GENE PRODUCT

CROSS REFERENCE TO RELATED APPLICATIONS

This is a Continuation of application Ser. No. 09/222,377, filed Dec. 29,1999, now abandoned, which claims priority to a Provisional application Ser. No. 60/071,727, filed Dec. 20, 1997.

PREFERENCE TO GOVERNMENT GRANT

The invention described herein was supported in part by National Institutes of Health grants RO1 CA39481 and RO1 CA47282. The U.S. government has certain rights in the invention.

BACKGROUND OF THE INVENTION

The control of cell proliferation is a central event in tumorigenesis and often depends on the interactions between growth factors and their specific receptor-activated signaling pathways. The nature of the local extracellular matrix modulates cellular responses to a given signal via various means, for example by affecting the affinity of the ligand for its cognate receptor and by influencing proteolytic processing and internalization (Iozzo, R. V. and A. D. Murdoch. 1996. FASEB J. 10:598–614).

There is increasing evidence that decorin (Krusius, T. and E. Ruoslahti. 1986. Proc. Natl. Acad. Sci. USA 83:7683–7687; Day, A. A. et al. 1987. Biochem. J. 248:801–805; Fisher, L. W. et al. 1989. J. Biol. Chem. 264:4571–4576), a member of an expanding gene family encoding small leucine-rich proteoglycans, plays an role in modulating cell proliferation, cell adhesion, cell migration, and collagen fibril formation. Decorin can bind in vitro to a variety of adhesive and nonadhesive proteins including fibronectin, thrombospondin, various types of collagens, and transforming growth factor-β (TGF-β; Iozzo, R. V. and A. D. Murdoch. 1996. FASEB J. 10:598–614). The binding of decorin to fibrillar collagen carries important biological implications as recently demonstrated by the phenotype of mice lacking the decorin gene (Danielson, K. G. et al. 1997. J. Cell Biol. 136:729–743). In these mutant animals, disruption of the decorin gene leads to skin fragility and abnormal collagen morphology, characterized by uncontrolled lateral fusion of fibrils. Binding of decorin to TGF-β prevents fibrosis of renal glomeruli by neutralizing its biological activity (Border, W. A. et al. 1992. Nature 360:361–364). Decorin cDNA was recently used as a gene therapy tool for treatment of fibrotic diseases caused by TGF-β (Isaka, Y. et al. 1996. Nat. Med. 2:418–423).

Decorin has also been implicated in the control of cell proliferation. Forced expression of decorin in Chinese hamster ovary (CHO) cells has been demonstrated to lead to decreased growth rate, lowered saturation density, and altered morphology (Yamaguichi, Y. and R. Ruoslahti. 1988. Nature 336:244–246). It has been suggested that decorin causes these changes in this cell system by sequestering TGF-β, an autocrine growth stimulator for these cells (Yamaguichi, Y. et al. 1990. Nature 346:281–284). Decorin is also markedly upregulated during quiescence in human diploid fibroblasts (Coppock, D. L. et al. 1993. Cell Growth Differ. 4:483493; Mauviel, A. et al. 1995. J. Biol. Chem. 270:11692–11700) and its expression is strongly suppressed upon viral transformation with SV40 (Coppock, D. L. et al. 1993. Cell Growth Differ. 4:483–493). Decorin is rarely expressed by malignant epithelial cells from a wide variety of human tumors including colon, pancreas, prostate, and breast carcinomas (Iozzo, R. V. and I. Cohen. 1993. Experientia 49:447–455). However, in the tumor stoma of colon cancer, the amount of decorin proteoglycan is increased markedly through a process that involves hypomethylation of the decorin gene (Adany, R. et al. 1990. J. Biol. Chem. 265:11389–11396) as well as induction of this gene product via tumor-secreted cytokines (Iozzo, R. V. 1985. J. Biol. Chem. 260:7464–7473).

Using a gene transfer approach in human colon carcinoma cells that do not constitutively express this gene, it was demonstrated that de novo expression of decorin reverted the cells to a normal phenotype. In these experiments, the cells lost anchorage-independent growth, failed to generate tumors in scid/scid mice, and became arrested in the $G_1$ phase of the cell cycle (Santra, M. et al. 1995. Proc. Natl. Acad. Sci. USA 92:7016–7020). This decorin-induced growth arrest was associated with a marked induction of $p21^{Waf1/cip1/sdi1}$ (p21), a potent inhibitor of cyclin-dependent kinase (CDK) activity (Harper, J. W. et al. 1993. Cell 75:805–816; El-Deiry, W. S. et al. 1993. Cell 75:817–825). Experiments also have shown that augmented p21 protein is present in a multimeric complex with various cyclins and CDKs in the nuclei of decorin-expressing clones and that its levels can be abolished by abrogating decorin expression (DeLuca, A. et al. 1996. J. Biol. Chem. 271:18961–18965).

It has now been found that administration of decorin to tumor cells results in suppression of the growth of tumor cells.

SUMMARY OF THE INVENTION

The present invention provides a method for suppressing tumor growth by administration of decorin, a proteoglycan.

According to one embodiment, a method for suppressing tumor cell growth in an animal comprises administering to an animal suffering from a tumor a decorin gene protein product so that tumor growth is suppressed in the animal. According to one preferred embodiment, the decorin gene product comprises wild-type decorin or Δdecorin. The decorin gene product is administered systemically according to one embodiment, and locally, to the tumor site, in other embodiments.

According to another embodiment, a method for suppressing tumor cell growth in an animal comprises administering to an animal suffering from a tumor a vector expressing a decorin gene protein product so that tumor growth is suppressed in the animal. According to one preferred embodiment, the vector expresses wild-type decorin or Δdecorin. The vector is preferably a retroviral vector or an adenoviral vector.

In one embodiment, the vector is administered to cells of the patient in vivo, either systemically or locally to the tumor site. According to another embodiment, the vector is administered to normal cells of the patient ex vivo to obtain over-expression of the decorin protein gene product by such cells. The cells are then returned to the body of the patient in the vicinity of the tumor.

According to one preferred embodiment, the tumor cells subject to treatment express epidermal growth factor receptors. According to another preferred embodiment, the tumor is characterized by a deleterious p53 mutation.

The animal treated according to the present invention is preferably a human being.

DESCRIPTION OF THE FIGURES

FIG. 1A represents Northern blotting analyses of total RNA extracted from G418-resistant Saos-2 osteosarcoma and murine M2 melanoma clones stably transfected with either decorin or Δdecorin. The values are normalized on GADPH. FIG. 1B represents Western blotting analyses of media conditioned for 24 hours by stably transfected human Saos-2 osteosarcoma, HeLa epidermal carcinoma, HT-1080 fibrosarcoma, HL-60 promyelocytic leukemia cells, and murine M2 melanoma cells, and probed with an antidecorin antibody directed against the amino terminal peptide.

FIG. 8A: (-○-), $Dcn^{-/-}$ (n=6); (-θ-), $Dcn^{+/+}$ (n=6). FIG. 8B: (-○-), $Dcn^{-/-}$ (n=6); (-●-), $Dcn^{+/+}$ (n=9). FIG. 8A also shows results in mice of a nonsyngeneic background (-▼-, FVB $Dcn^{-/-}$ (n=6)). All values are the average with SD<15% of the mean.

DETAILED DESCRIPTION OF THE INVENTION

Introduction

Figures 1A, 1B:
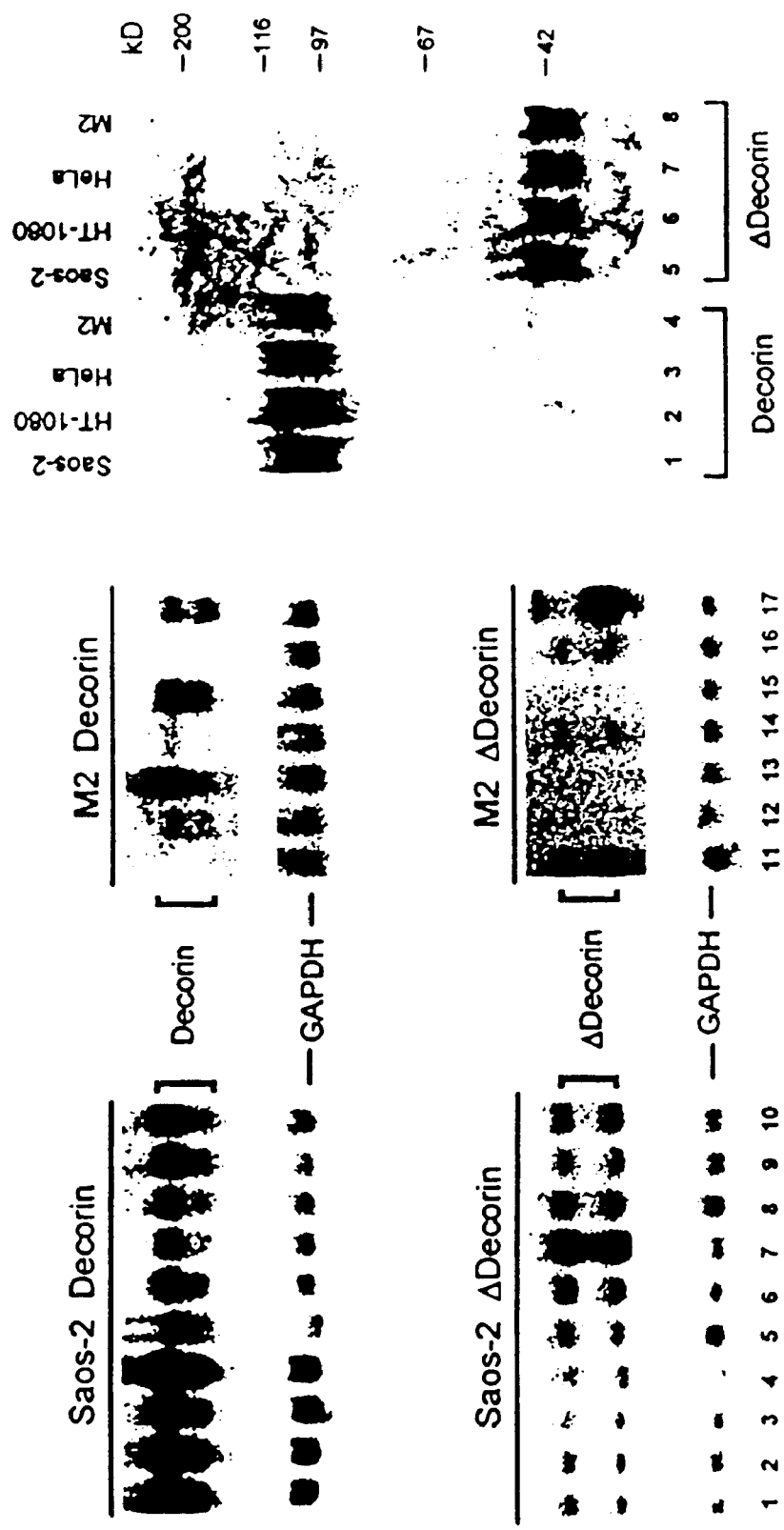
FIGS. 1A and 1B show the expression of decorin in various stably-transfected tumor cell lines.

Recent advances in understanding the biochemistry and biology of tumor extracellular matrix indicates a role for matrix proteins in regulating cancer growth (Iozzo, R. V. 1995. *Lab. Invest.* 73:157–160). However, to understand and potentially inhibit the means that guide tumor cells to invade host tissues, the interactions between matrix proteins and tumor cells must be understood. It has now been found that decorin induces activation of epidermal growth factor receptor thereby resulting in inhibition of cell proliferation. Accordingly, in the present invention a method is provided for suppressing tumor cell growth by administering decorin, or a vector encoding decorin.

According to the present invention, transfection of with the full length proteoglycan decorin, or decorin protein core (Δdecorin) induces a marked and protracted growth suppression and concurrent induction of p21 mRNA in tumor cells. Exogenous decorin has the same effect. The decorin-induced growth suppression is mediated by decorin binding to epidermal growth factor (EGF) receptor, a transmembrane glycoprotein with an extracellular ligand-binding domain and an intracellular tyrosine kinase domain whose activity is induced by EGF. Decorin and Δdecorin induce rapid tyrosine phosphorylation of the EGF receptor (EGFR), concomitant activation of mitogen-activating protein (MAP) kinases, and finally induction of endogenous p21.

The EGF receptor is a site at which decorin initiates a rapid and sustained activation of the MAP kinase signal transducing pathway, resulting in prolonged induction of endogenous p21 and ultimately growth arrest. Signaling takes place through EGFR dimerization. Decorin interacts specifically with the EGFR ectodomain. Decorin binds purified EGFR with a $K_d$ of about 87±7.5 mM. The activity of decorin on EGFR results in mobilization of intracellular calcium, a specific mechanism by which decorin can cause growth suppression. By directly interacting with tumor cell receptors such as EGFR, decorin influences the outcome of abnormal cell proliferation.

It has been found that the lack of decorin expression alone does not predispose to tumor formation, but its absence favors cancer growth and invasion. It is further demonstrated herein that the combination of a tumor suppressor (e.g., p53) deficiency and decorin deficiency predisposes an individual to an accelerated mortality due to enhanced tumorigenesis.

The growth of cancerous cell is significantly inhibited when ectopic expression of decorin is induced, or when exogenous decorin is introduced.

Accordingly, the present invention provides a method of suppressing growth of a variety of tumor cell types. In this method a decorin gene protein product can be administered directly to an animal suffering from a tumor. Alternatively, a vector comprising a decorin gene or portion thereof which expresses a decorin gene protein product can be administered as a gene therapy agent which increases levels of expressed decorin in the animal. Administration of a decorin gene protein product directly or as a gene therapy agent results in activation of EGF receptor function in tumor cells, thereby leading to growth suppression. The method of the present invention may also be useful in delaying metastasis or following surgical removal of a tumor to prevent recurrence.

Definitions and General Methodology

The following definitions are intended as an aid to understanding the scope and practice of the present invention.

By "animal" it is meant to include, but is not limited to, mammals including humans.

"Decorin gene" is used to describe the gene of the aforementioned name, and all allelic forms, both naturally occurring and created in the laboratory, without regard to the species of origin. By way of example, and not by way of limitation, "decorin gene" includes not only the wild-type gene, but also a mutant form wherein the codon TCT of the decorin cDNA encoding the amino acid $Ser^7$ of the mature protein core is mutated into GCT (Ala). The Ser-7 holds the glycosaminoglycan sugar chain in the decorin molecule. This mutanized decorin (Δdecorin) is secreted as the core protein with no detectable glycosaminoglycan side chain (Mann et al., *J. Biol. Chem.* 1990. 265:5317–5323).

"Decorin", "decorin protein" or "decorin gene product" all are meant to describe the polypeptide that is encoded by the decorin gene. The terms include the wild-type decorin protein, as well as other forms, both naturally occurring and created in the laboratory. Thus, included is the full length wild-type decorin protein or a natural or mutagenized fragment thereof, e.g. Δdecorin, which is capable of activating an EGF receptor and suppressing cell proliferation.

A "deleterious mutation" with respect to a gene means a mutation which impairs the function of the gene or the encoded gene product.

A "vector" is any means for the transfer of a nucleic acid into a host cell. The term vector includes both viral and nonviral means for introducing the nucleic acid into a prokaryotic cell in vitro, ex vivo, or in vivo. Non-viral vectors include but are not limited to plasmids, liposomes, electrically charged lipids (such as cytofectins), DNA-protein complexes, and biopolymers. Viral vectors include but are not limited to vectors derived from retrovirus, adeno-associated virus, pox viruses, baculovirus, vaccinia virus, herpes simplex virus, Epstein-Barr virus, adenovirus and hybrids of two or more viral vector types. In addition to an antiviral construct according to the invention, a vector may contain one or more regulatory regions, and/or selectable markers useful in selecting, measuring, and monitoring nucleic acid transfer results (transfer to which tissues, duration of expression, etc.).

"Pharmaceutically acceptable carrier" includes diluents and fillers which are pharmaceutically acceptable for method of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation. Generally enzymatic reactions, oligonucleotide syntheses, and purification steps are performed according to the manufacturer's specifications. The techniques and procedures are generally performed according to conventional methods in the art and various general references which are known to the skilled artisan, including Maniatis (Molecular Cloning, Cold Spring Harbor Laboratories, 1982), and Ausubel (Current Protocols in Molecular Biology, Wiley and sons, 1987), which are incorporated herein by reference.

Vectors and Methods of Gene Delivery

The human decorin gene can be used as a gene therapeutic to inhibit or suppress the tumor cell growth and thereby provide a favorable therapeutic outcome in patients afflicted with such tumor growth.

The decorin gene is preferably delivered to the patient in the form of a vector. In a preferred embodiment, the decorin gene becomes stably integrated into the cellular genome.

Non-viral vectors may be transferred into cells using any of the methods known in the art, including calcium phosphate coprecipitation, lipofection (synthetic anionic and cationic liposomes), receptor-mediated gene delivery, naked DNA injection, electroporation and bioballistic or particle acceleration. Viral vectors may be transferred into cells using any method known in the art, including infection and transfection.

Viral vectors that may be used in the present invention include adenoviral vectors and retroviral vectors, with the latter being preferred.

Adenoviruses are eukaryotic DNA viruses that can be modified to efficiently deliver nucleic acid to a variety of cell types. Various serotypes of adenovirus exist, including type 2 and type 5 human adenoviruses and adenoviruses of animal origin. Preferably, the replication defective adenoviral vectors according to the invention comprise the ITRs, an encapsidation sequence, and the nucleic acid of interest. Still more preferably, at least the E1 region of the adenoviral vector is nonfunctional. Other regions may also be modified, including the E3 region (see WO95/02697), the E2 region (see WO94/28938), the E4 region (see WO94/28152, WO94/12649, and WO 95/02697), or in any of the late genes L1–L5.

Replication defective recombinant adenoviruses can be prepared by techniques known to a person skilled in the art. In particular they can be prepared by homologous recombination between an adenovirus and a plasmid which carries the DNA sequence of interest. Homologous recombination is effected following cotransfection of the adenovirus and plasmid into an appropriate cell line. The cell line employed should be transformable by said components and contain sequences which are able to complement the defective regions in the replication defective adenovirus. Examples of cell lines which may be used are the human embryonic cell line 293 (Graham et al., *J. Gen. Virol.* 36, 59 (1977)) which contains the left-hand portion of the genome of an Ad5 adenovirus (12%) integrated into its genome, and cell lines which are able to complement the E1 and E4 functions, as described in WO94/26914 and WO95/02697. Recombinant adenoviruses are recovered and purified using standard biological techniques which are well known to those having ordinary skill in the art.

One class of useful adenovirus vectors may be prepared according to Bett et al., *Proc. Natl. Acad. Sci. (USA)* 91:8802–6 (1994), which describes a system for construction of adenovirus vectors with insertions or deletions in the E1 and E3 regions.

Adenoviral vectors can be produced at high titers (e.g. $10^{10}$–$10^{12}$ infectious units per ml), and can be used to transiently express decorin in infected target cells.

Retroviruses are integrating viruses which generally infect dividing cells. The retrovirus genome includes two long terminal repeats (LTRs), an encapsidation sequence and three coding regions (gag, poland env). The construction of recombinant retroviral vectors is known to those of skill in the art.

In recombinant retroviral vectors, the gag, pol, and env-genes are generally deleted, in whole or in part, and replaced with a heterologous nucleic acid sequence of interest. These vectors can be constructed from different types of retrovirus, such as M-MuLV, MSV (murine Moloney sarcoma virus), HaSV (Harvey sarcoma virus), SNV (spleen necrosis virus), RSV (Rous sarcoma virus) and Friend virus.

In general, in order to construct recombinant retroviruses containing a sequence according to the invention, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art. In particular the cell line PA317 (U.S. Pat. No. 4,861,719), the PsiCRIP cell line (WO90/02806), and the GP+envAm-12 cell line (WO89/07150) may be mentioned. Recombinant retroviral vectors are purified by standard techniques known to those having ordinary skill in the art.

Retroviral vectors derived from lentiviruses such as HIV-1, HIV-2, and SIV can be used for delivery to nondividing cells. These viruses can be pseudotyped with the surface glycoproteins of other viruses, such as M-MuLV or vesicular stomatitis virus (VSV). The production of high titer HIV-1 pseudotyped with VSV glycoprotein has been disclosed by Bartz and Vodicka, *Methods* 12(4):337–42 (1997), and multiply attenuated lentiviral vectors have been disclosed by Zufferey et al., *Nature Biotechnology* 15:871–75 (1997). Such lentiviral vectors can infect nondividing cells, have a broad host range, and can be concentrated to high titers by ultracentrifugation.

Chimeric adenoviral/retroviral vector systems can also be used to achieve efficient gene delivery and long term gene expression. A chimeric viral system in which adenoviral vectors are used to produce transient retroviral producer cells in vivo, such that progeny retroviral particles infect neighboring cells has been described by Feng etal., *Nature Biotechnology* 15:866–70 (September 1997).

Expression vectors encoding decorin can be generated in several ways using standard techniques of molecular biology. The vector should be suitable for stable, high-level expression of decorin in mammalian cells. Retroviral vectors containing strong viral promoters, such as the immediate-early human cytomegalovirus(CMV)/enhancer, to drive the expression of the inserted decorin gene is the preferred vehicle for the decorin gene transfer.

The preparation of suitable decorin and Δdecorin transfection constructs is described in Santra, M. et al. 1995. *Proc. Natl. Acad. Sci. USA* 92:7016–7020 and Santra et al., (1997) *J. Clin. Invest.* 100:149–157, the entire disclosures of which are incorporated herein by reference. Briefly, a modified full-length decorin cDNA is digested with EcoRi, then digested BamHI, and finally ligated to the 3' end of the human CMV early gene promoter/enhancer in a mammalian expression vector pcDNA3 (Initrogen Corp., San Diego, Calif.).

Vectors encoding expression of decorin are administered to a patient in an amount sufficient to treat or prevent the occurrence of tumor growth. Effective amounts vary depending on the characteristics of the patient, the type and severity of the condition being treated, the desired duration of treatment, the method of administration, and other parameters.

Effective amounts may be determined by the physician or by another qualified medical professional. Recombinant viruses are generally formulated and administered in the form of doses of from about $10^4$ to about $10^{14}$ pfu, more preferably from about $10^6$ to about $10^9$, most preferably from about $10^6$ to about $10^8$.

Vectors encoding decorin expression may be administered systemically, such as by intravenous administration. Alternatively, the vector is administered locally such as by subcutaneous injection directly into a tumor, or into normal tissue surrounding the tumor. The production of decorin by the transfected cells may be verified by sampling the tissues and measuring decorin expression by conventional means (e.g., Northern or Western blotting).

As an alternative to in vivo vector delivery to a tumor or tumor site, normal cells may be excised from the patient and transfected ex vivo to enhance decorin expression. The decorin over-expressing cells are then reimplanted in the body of the patient, at a site proximal to the tumor sought to be treated. In this manner, decorin is released to the tumor, to secure therapeutic benefit. For this type of ex vivo transfection, the vector may take the form of a simple expression vector, such as the construct described by Santra et al., (1997) *J. Clin. Invest.* 100:149–157 (decorin cDNA ligated to 3 end of human CMV early gene promoter/enhancer in mammalian expression vector pcDNA3). Skin fibroblasts are the preferred host cells for ex vivo decorin transfection with a decorin over-expressing construct and return to the host.

Vector administration is carried out and repeated on a monthly basis, or more frequently, depending on the stability of the transfection.

Administration of Decorin Protein

Decorin gene products are administered to a patient in an amount sufficient to treat or prevent the occurrence of tumor growth. Effective amounts vary depending on the characteristics of the patient, the type and severity of the condition being treated, the desired duration of treatment, the method of administration, and other parameters. Effective amounts may be determined by the physician or by another qualified medical professional.

Decorin gene products may be administered systemically or locally to suppress or inhibit tumor growth in an infected individual. The protein may be administered systemically. Human full length recombinant decorin or Δdecorin is preferred. As these are human proteins, no immune reaction by the host is expected. Moreover, decorin is a highly soluble in aqueous solutions. Thus, the preferred vehicle for therapeutic use is an aqueous vehicle, such as a sterile saline.

For systemic administration, the decorin protein may be administered in a dosage of from about 1 to about 1,000 mg per 70 kg human patient, more preferably from about 1 to about 100 mg, most preferably from about 10 to about 50 mg. Other dosages are contemplated, depending on the condition of the patient, the nature and extent of the neoplasm, and other factors. The recommended dosage may be give once per week, over a treatment period lasting from 4 to 8 weeks. Other treatment regimens are also contemplated. The treatment regimen may be repeated as necessary.

As an alternative to systemic administration, the decorin protein is administered locally such as by subcutaneous injection directly into a tumor, or into normal tissue surrounding the tumor. The dosage for local administration may range, for example, from about 0.1 to about 100 mg, preferably from about 0.1 to about 10 mg, most preferably from about 0,5 to about 5 mg.

The decorin protein is contained in a pharmaceutically acceptable carrier. Such carriers include physiologically tolerable or acceptable diluents, excipients, solvents, adjuvants, or vehicles, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isosteraryl alcohols, polyoxyethylene sorbitol and sorbitan esters, microcrystalline cellulose, aluminum methahydroxide, bentonite, agar-agar and tragacanth, or mixtures of these substances, and the like.

Pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

Compositions containing the decorin protein may be administered by any convenient route which will result in delivery to the site of the tumor an amount effective for inhibiting that tumor's growth. Modes of administration include, for example, orally, rectally, parenterally (intravenously, intramuscularly, intraarterially, or subcutaneously), intracisternally, intravaginally, intraperitoneally, locally (powders, ointments or drops), or as a buccal or nasal spray or aerosol. The compositions can also be delivered through a catheter for local delivery at a target site, or via a biodegradable polymer. The compositions may also be complexed to ligands, or antibodies, for targeted delivery of the compositions.

The compositions are most effectively administered parenterally, preferably intravenously or subcutaneously. For intravenous administration, they may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution.

Disease Conditions Treated

Decorin gene therapy or administration of decorin gene products may be utilized to treat any neoplastic disease. Preferably, the treatment is carried out on individuals suffering from a neoplastic disease characterized by the occurrence of one or more solid tumor masses. Tumors treatable include, for example, osteosarcoma; fibrosarcoma; colon carcinoma;

melanoma; epidermal carcinoma; breast carcinoma; various forms of brain carcinoma, such as glioblastoma, for example; lung carcinoma; pancreatic carcinoma; prostate carcinoma; testicular carcinoma; various gynecological carcinomas such as ovarian carcinoma and endometrial carcinoma; head and neck carcinoma; carcinoma of the oral cavity, throat or stomach. Moreover, the treatment may be undertaken for solid tumors which may arise from leukemias and lymphomas.

Throughout the course of therapy, the patient is preferably monitored to 10 assess the treatment effectiveness. The primary indicia of treatment success is tumor shrinkage. The size of the tumor treated may be monitored over the course of the therapy by well-known tumor imaging techniques such as x-ray, CAT scan, magnetic resonance imaging, direct visual or microscopic examination where feasible, and the like.

Ectopic Expression of Decorin or Protein Core Causes Tumor Cell Growth Suppression via Activation of Endogenous p21

Experiments were performed to determine specific pathways in cells that are affected by decorin gene products. The involvement of epidermal growth factor (EGF) receptor in the decorin-specific effects on cell proliferation was examined. EGF can be stimulatory in several normal and malignant cells, but the proliferation of certain cells is inhibited by this growth factor (Barnes, D. W. 1982. *J. Cell Biol.* 93:1–4). Human A431 squamous carcinoma cells were selected for testing since they express a high number of EGF receptors (approximately $2 \times 10^6$/cell) and their growth is suppressed by exogenous EGF (Fan, Z. et al. 1995. *J. Cell Biol.* 131:235–242). A431 cells were stably transfected with either full length decorin or Δdecorin by methods known to those of skill in the art (Santra, M. et al. 1995. *Proc. Natl. Acad. Sci. USA* 92:7016–7020). Cell proliferation assay and Northern and Western blottings were performed as previously described (Santra, M. et al. 1995. *Proc. Natl. Acad. Sci. USA* 92:7016–7020). Antibodies used in immunoblots included the anti-phosphotyrosine monoclonal antibody PY20 (Transduction Laboratories), the anti-EGF receptor monoclonal antibody (Promega Corporation), and the mouse monoclonal 6B6 antibody directed towards human p21 (PharMingen). Quantitation of immunoblots was performed with a PhosphorImager 445SI (Molecular Dynamics). Decorin was purified from the secretions of CHO cells transfected with a full length decorin-expressing vector as described by Yamaguichi, Y. and E. Ruoslahti. 1988. *Nature* 336:244–246. Recombinant decorin proteoglycan, decorin protein core, or biglycan purified from HT-1080 fibrosarcoma cells infected with a recombinant vaccinia virus were also used (Hocking, A. M. et al. 1996. *J. Biol. Chem.* 271:19571–19577; Ramamurthy, P. et al. 1996. *J. Biol. Chem.* 271:19578–19584). All the recombinant preparations tested for biological activity contained undenatured protein cores and the final products were tested for purity by SDS-PAGE and immunoblotting, methods well known to those of skill in the art.

Routinely, cells were serum-starved overnight and lysed without stimulation, or after treatment with either 50–100 μg/ml decorin, decorin protein core, or biglycan, or with 100 ng/ml EGF. Cell lysates were subjected to immunoprecipitation with either alpha-pTyr or alpha-EGF receptor antibodies followed by separation by SDS-polyacrylamide gels (PAGE) and immunoblotting. The Cell Titer 96™ Aqueous Non-Radioactive Cell Proliferation Assay (Promega Corporation) was used to determine the number of viable cells in a proliferative phase. Decorin was labeled with [$^{125}$I]NaI (Amersham) to a specific activity of $8 \times 10^6$ cpm/μg using the Iodo-Gen method (Pierce Chemical Co.) according to the manufacturer's protocol. A431 cells were plated in 16 mm wells, grown for 2 days to near confluence, washed twice with buffer, and the wells blocked with 1 mM RPMI 1640 containing 0.2% BSA for one hour at 4° C. The medium was removed, and the cells were incubated in a 0.5 ml 0.2% BSA/RPMI1640 containing approximately 200 ng ($1.5 \times 10^6$ cpm) radiolabeled decorin and various concentrations of EGF. After two hours on ice, the wells were washed three times with cold buffer, the cells dissolved in 1 ml/well 1 mM NaOH, and the radioactivity measured in a gamma counter.

Results from these experiments showed that transfection with either full length decorin or Δdecorin induced a marked and protracted growth suppression and a concurrent induction of p21 mRNA. A significant induction of endogenous p21 mRNA levels was also obtained when wild-type A431 cells were cultured in the presence of highly purified human recombinant decorin isolated from either HT-1080 fibrosarcoma cells or CHO cells. The kinetics of growth inhibition were consistent with the time course induction of p21 protein by exogenous decorin.

Exogenous Decorin or Decorin Protein Core Causes Growth Suppression and p21 Induction Experiments were also performed to examine the effect of exogenous decorin o decorin protein core on growth suppression and p21 induction. In these experiments, A431 cells were incubated in the absence or presence of decorin, its protein core, or biglycan, a related proteoglycan. It was found that the core protein of decorin was capable of inducing a protracted growth suppression and a concurrent induction of endogenous p21. In contrast, equimolar amounts of recombinant biglycan were essentially ineffective. A different preparation of human recombinant decorin synthesized by CHO cells required at least 24 hours to produce a noticeable effect. In addition, a fusion protein containing decorin and the maltose binding protein of E. coil was totally ineffective in inducing growth suppression. Thus, the growth suppression in A431 cells is specifically mediated by the protein core of decorin. Further, these data indicate that this suppression requires proper protein folding for full biological activity since the inactive prokaryotic form of decorin presumably lacks disulfide bonds at both the amino and carboxyl ends of the molecule (Ramamurthy, P. et al. 1996. *J. Biol. Chem.* 271:19578–19584).

Decorin Induces Phosphorylation of the EGF Receptor and Concomitant MAP Kinase Activation Experiments were then performed to determine whether EGF receptor itself mediated the decorin-induced growth suppression. The EGF receptor is a transmembrane glycoprotein with an extracellular ligand-binding domain and an intracellular tyrosine kinase domain whose activity is induced by EGF (Schlesinger, J. and A. Ullrich. 1992. *Neuron* 9:383–391). The tyrosine-phosphorylated EGF receptor binds to modular signal proteins and eventually leads to activation of mitogen-activating protein (MAP) kinases ERK1 and ERK2, two members of highly conserved enzymes involved in responses to extracellular signals (Seger, R. and E. G. Krebs. 1995. *FASEB J.* 9:726–735). Phosphorylation of both threonine and tyrosine residues in a TxY sequence common to most MAP kinases is required for their full activation (Seger, R. and E. G. Krebs. 1995. *FASEB J.* 9:726–735) and this phosphorylation can be detected as a shift toward higher $M_T$ in SDS-PAGE. Highly purified recombinant decorin induced tyrosine phosphorylation of a 170 kDa protein in a dose-dependent manner within 5 minutes suggesting direct activation of the receptor. Decorin-induced activation of the 170 kDa protein co-migrating with the EGF receptor was associated with a slower migrating form of p42 MAP kinase (ERK2), thereby signifying MAP kinase activation.

Decorin Binds to the EGF Receptor and its Activation is Prevented by Inhibitor of EGF Receptor Tyrosine Kinase To more directly assess whether decorin binds to the EGF receptor, A431 cells were incubated with a constant amount (20 ng) of radiolabeled recombinant decorin and then with increasing amounts of unlabeled EGF. A significant partial displacement of the bound decorin was observed using relatively high dosages of EGF (300 ng). The partial displacement is believed to result from the known ability of decorin to bind to a variety of bioactive molecules.

The specificity of decorin/EGF receptor interaction was further tested by additional experiments. Exogenous decorin protein core was as effective as exogenous proteoglycan in inducing phosphorylation of the 170 kDa protein. Equimolar amounts of recombinant human biglycan were essentially ineffective, indicating the effects were specific to decorin.

Decorin also caused low levels of EGF receptor activation of MAP kinase. The causal role of cell surface receptors in MAP kinase activation by decorin or EGF was assessed. Tyrphostin AG1478, a quinazoline specific inhibitor of EGF receptor tyrosine kinase was used (Levitzki, A. and A. Gazit. 1995. *Science* 267:1782–1788). In these experiments a concentration of AG1478 that is one fiftieth of that required to inhibit c-src kinase (Levitzki, A. and A. Gazit. 1995. *Science* 267:1782–1788) effectively blocked activation of the EGF receptor kinase and MAP kinase caused by either EGF or exogenous decorin. In contrast, MAP kinase activation by platelet-derived growth factor was unaffected by the same concentrations of AG1478. Sequential immunoprecipitation with antibodies against phosphotyrosine followed by immunoblotting with antibodies against EGF receptor, or the reciprocal experiment, demonstrated that the 170 kDa protein phosphorylated in response to decorin is the EGF receptor.

To determine whether the decorin-induced growth suppression was mediated, at least in part, through the EGF receptor pathway, A431 cells were grown in the presence or absence of exogenous decorin or Δdecorin with or without 2 μM AG1478. Results from these experiments demonstrated that the growth inhibitory activity of decorin and Δdecorin could be significantly blocked by tyrphostin.

Decorin Causes Phosphorylation of EGF Receptor. MAP Kinase Activation, and p21 Induction in Cells of Diverse Histogenetic Background Additional cell lines were also tested that lacked either the EGF receptor (AGS gastric carcinoma cells) or that expressed unusually high levels ($4\times10^6$/cell) of the receptors (HNSCC head and neck carcinoma cells). Murine NIH3T3 fibroblasts (CO12 cells) which had been transfected with the human EGF receptor cDNA ($4\times10^5$ receptors/cell) were used and compared with their wild-type counterparts which express very low levels of EGF receptor (Moscatello, D. K. et al. 1996. *Oncogene* 13:85–96). As expected for a decorin-EGF receptor interaction, decorin induced a MAP kinase shift in all the cell lines in which EGF receptor phosphorylation was observed (LTRb2, CO12, and HNSCC), but not in the AGS cells, which exhibited no response to EGF. The induced levels of p21 correlated well with the EGF receptor phosphorylation and MAP kinase activation in the responsive cells. Additional cell lines were tested for p21 induction and AG1478 block and compared to the A431 parental cells. In all the cells, including Saos-2 osteosarcoma, HT-1080 fibrosarcoma and HeLa cervical carcinoma cells, decorin-dependent induction of endogenous p21 was partially or totally blocked by AG1478. The signal transducers and activators of transcription, STAT1 and STAT3, have been implicated in the induction of p21 by EGF in some cell lines (Chin, Y. E. et al. 1996. *Science* 272:719–722). However, STAT1 activation was only observed in some of the cell lines in which decorin induced p21, in contrast to the ubiquitous activation of MAP kinase, suggesting a role for STAT proteins in p21 induction in only certain cell types. Thus, it is believed that EGF receptor (EGFR) is a site at which decorin initiates a signaling cascade that leads to induction of endogenous p21 and ultimately to growth arrest.

Further experiments were conducted to investigate whether decorin induces rapid and sustained activation of the MAP kinase signal transducing pathway. Quiescent A431 cells were exposed to 1 μM decorin or its protein core for either 18 hours or 10 minutes. EGF (16 nM) or collagen (1 μM) were used as positive and negative controls, respectively. Total cell lysates were separated by SDS-PAGE and transferred to nitrocellulose membranes as described before (Santra et al., (1997) *J. Clin. Invest.* 100:149–157). The anti-phospho-MAP kinase antibody (New England BioLabs) detects p42 and p44 MAP Kinases (Erk1/Erk2) only when they are catalytically activated by phosphorylation at amino acids $Thr^{202}$ and $Tyr^{204}$. A sustained and rapid activation of the MAP kinase signal pathway resulted, which leads to prolonged activation of the endogenous p21 end block of the cells in G1.

To more directly investigate the interaction between the EGFR and decorin, EGFR purified by immunoaffinity chromatography from plasma membranes of A431 cells was employed (Yarden et al., (1985) *J. Biol. Chem.* 260: 315–319). The EGFR was not exposed to EGF during the purification procedure. Thus, it contained optimal kinase activity and was suitable for both binding and in vitro kinase assays. The purity of the EGFR and the lack of degradation products was established by Western immunoblotting. A single ~170 kDa band was seen using an antibody against the N-terminus of the EGFR.

The EGFR was then subjected to in vitro kinase assay in the presence of decorin, its protein core or collagen. Accordingly, constant amounts (~300 ng) of immunopurified EGFR were preincubated with buffer alone or containing increasing concentrations (5–20 $\mu$g) of decorin, its decorin protein core, or collagen type 1. After 15 minutes incubation in kinase buffer (20 mM HEPES, pH 7.4, 2 mM $MnCl_2$, 10 mM p-nitrophenyl phosphate, 40 $\mu$M $Na_3VO_4$, 0.01% BSA, 15 $\mu$M ATP) 1 $\mu$Ci [$\gamma$-$^{32}$P]ATP and 0.2% NP40 were added to reach a final volume of 60 $\mu$l. The mixture was incubated for an additional 10 minutes, the reaction was stopped by boiling in SDS buffer and analyzed by SDS-PAGE. Phosphorylated proteins were visualized by autoradiography. Control samples omitting either [$\gamma$-$^{32}$P]ATP or EGFR showed no activity.

There was a dose-dependent induction of EGFR autophosphorylation only in the presence of decorin or its protein core, but none in the presence of collagen. Of note, the EGFR kinase efficiently phosphorylated decorin protein core as seen by the appearance of the two ~42 and 46 kDa proteins seen only when the protein core was added. No significant phosphorylation of the decorin proteoglycan (which would have appeared as a ~100 kDa band) was noted indicating that the actual phosphorylation of the protein core may be inhibited by the dermatan sulfate chain. The presence of EGFR tyrosine kinase-dependent phosphorylation of the decorin protein core is compatible with the presence of eight tyrosine residues (Iozzo et al. (1998) *Annu. Rev. Biochem.* 67:609–652). The binding of decorin to the EGFR was totally abolished by heat denaturation (80° C. for 15 min.) of both decorin and its protein core. The same treatment of the EGFR abolished the binding to decorin. Thus, proper protein folding is required for this interaction.

Decorin and its Protein Core Cause EGF Receptor Dimerization

To further investigate the pathway of decorin-induced growth suppression, test were conducted to determine whether signaling might take place by EGF receptor dimerization. To test this, purified decorin proteoglycan or its protein core (100 $\mu$g/ml) was added to quiescent A431 cells at 4° C. for 1 hour washed extensively and incubated for 30 min with $BS^3$ (Bis[sulfosuccinimidyl]suberate), a noncleavable, membrane impermeable cross-linker. The cell lysates were separated in a 3–15% SDS-PAGE and subjected to Western immunoblotting (Moscatello et al., (1998) *J. Clin. Invest.* 101:406–412) with anti-EGFR antibody. Decorin induced significant dimerization of the EGFR, estimated to be ~40% of that induced by EGF. There were no additive effects when decorin or its protein core were added concurrently with EGF. The protein core of decorin was capable of mediating the full effect of the decorin proteoglycan.

Decorin Interacts with the Soluble Ectodomain of the EGFR Receptor

To further explore the interaction of decorin and EGFR, experiments were conducted to identify the decorin binding site on EGFR.

The rationale for these studies is based on the observation that A431 cells synthesize and release into the medium a soluble form of EGFR of ~105 kDa lacking the transmembrane and intracytoplasmic domains (Weber et al. (1984) *Science* 224:294–297; Weber et al. (1984) *J. Bio. Chem.* 259: 14631–14636). This soluble protein is a variant derived from the 2.8 kb mRNA transcribed from a rearranged EGFR gene on chromosome 7 (Carpenter, G. (1987) *Ann. Rev. Biochem.* 56:881–914). As the extracellular domain has both a high Cys content (up to 25 disulfides are possible) and large amount of oligosaccharides, the ectodomain is quite stable and highly resistant to proteolysis. It binds with high affinity EGF (Weber et al. (1984) *Science* 224:294–297; Weber et al. (1984) *J. Biol. Chem.* 259:14631–14636), and available stochiometry data show that one mole of EGFR binds one mole of EGF. The synthesis of the soluble EGFR by A431 cells is comparable to that of the EGFR itself, and is equivalent to 5–7 pmol/$10^6$ cells/24 hr (Weber et al. (1984) *Science* 224:294–297).

First, the purity of the medium conditioned for 48 hrs by A431 cells was tested by performing Western immunoblotting. A single band of ~105 kDa was detected using the anti-EGFR antiserum. This material was used in slot-blot overlay assays in which both proteins (the immobilized and the soluble ligand) are under native conditions. Serum-free media conditioned for 48 hours by A431 cells was concentrated ~8 fold by centricon-50 and incubated with native decorin, its protein core or BSA immobilized on nitrocellulose filters, washed and subjected to immunodetection with anti-EGFR antiserum (Shrivastava et al., (1997) *Mol. Cell* 1:25–34). Both decorin protein core and decorin bound specifically to soluble EGFR ectodomain, in contrast to BSA which was unreactive. Chimeric biglycan/decorin protein containing the N-terminus of biglycan and the remaining decorin gave identical results. Thus, the binding to EGFR is not mediated by the N-terminus since biglycan does not cause activation of EGFR (Moscatello et al., (1998) *J. Clin. Invest.* 101:406–412). When similar slot blot overlay assays were tested with mAB 225, a monoclonal antibody that reacts specifically with the EGF binding region of the EGFR (Fan et al., (1994) *J. Bol. Chem.* 269:27595–27602), there was no reactivity, suggesting that decorin might bind near or perhaps in the same location where EGF binds.

To further corroborate the above results, scalar amounts of media conditioned for various periods of time by A431 cells were immobilized on nitrocellulose and subjected to overlay assays with soluble decorin followed by Western immunoblotting using an antibody that recognizes the N-terminal region of decorin (Fisher et al., (1995) *Acta Orthop. Scand.* 66:61–65). The results showed specific binding of decorin to serum-free medium conditioned by A431 cells which contains the EGFR ectodomain. Either DMEM or scalar dilutions of purified decorin were used as negative and positive controls, respectively. Taken together, these results show that decorin interacts specifically with the ectodomain.

Decorin Interacts with Purified EGF Receptor

Experiments were conducted to investigate whether soluble decorin could interact specifically with the EGFR under physiological salt concentrations and in solution.

Decorin contains an N-terminal 6xHis tag that allows a rapid and efficient purification via nickel-nitrilotriacetic acid (Ni-NTA) affinity chromatography (Ramamurthy et al., (1996) *J. Biol. Chem.* 271:19578–19584). Constant amounts of $^{32}$P-labeled EGFR, which was labeled using the same in vitro kinase assay described above, were incubated with increasing concentrations of decorin or its core protein for 30 minutes at 4° C. under gentle agitation. The Ni-NTA spin columns were equilibrated with 3 column volumes of binding buffer (300 mM NaH$_2$PO$_4$, pH 8.0, 300 mM NaCl), and then the samples were applied and spun at 750 g for 5 minutes. The Ni-NTA columns were equilibrated with 3 column volumes of binding buffer, and then the samples were applied and spun at 750 g for 5 minutes. Following two consecutive washes, the bound decorin/EGFR complexes were eluted with buffer containing 250 mM imidazole. Part of the fractions were counted in a scintillation counter and part were analyzed by SDS-PAGE and autoradiography. In two independent experiments there was specific binding of the EGFR to decorin since the amount of radioactive EGFR increased proportionally to the amount of interacting (Ni-NTA bound) decorin. Quantization of both experiments gave a strong correlation with $r^2=0.961$ and $P<0.0005$.

To determine more precisely the binding affinity, a radioligand binding assay was employed where increasing concentrations of $^{32}$P-labeled EGFR were tested on Immulon wells coated with decorin protein core (22 pmol). Binding of EGFR to decorin protein core was saturable and Scatchard plot gave a single straight line with $K_d$~87±7.5 nM (n=5). In parallel experiments where 10-fold more decorin protein core was used to coat the wells, the binding of EGFR was rapidly saturable and the data also yielded linear Scatchard plots. Notably, the affinity constant obtained in such experiments was ~9 fold lower than that reported for the low affinity binding sites for EGF (~10 nM) and ~90 fold lower than the high affinity receptor for EGF (~1 nM) (Carpenter et al., (1987) *Ann. Rev. Biochem.* 56:881–914).

Decorin Activates EGF Receptor and Elevates Cytosolic Ca$^{2+}$ in Tumor Cells

Additional experiments were performed to examine the activity of decorin on the EGF receptor. Since EGF receptors couple to phospholipase C, an enzyme that when activated leads to activation of calcium channels located within the intracellular storage compartments of intracellular calcium stores, the effect of decorin on calcium levels inside cells was examined. Increases in cytosolic calcium are associated with a wide range of cellular processes. The effects of decorin were examined in individual fura-2-loaded A431 cells. Such experimental methods are well known to those of skill in the art. Decorin increased intracellular cytosolic calcium levels in 49% of cells tested from a resting levels of 30 nM to a peak of 123 nM. Similar responses were observed after removal of calcium from the extracellular medium. These data indicate that decorin mobilizes calcium primarily from intracellular stores as opposed to directly stimulating calcium entry across the plasma membrane. These effects of decorin were shown to be specific to EGF receptor interactions as the effects were blocked by AG1478, the EGF-specific tyrosine kinase inhibitor as well as by down-regulation of the EGF receptor. Further, the effects of decorin were not mimicked by the structurally homologous protein, biglycan. Therefore, the activity of decorin on the EGF receptor results in mobilization of intracellular calcium, a specific mechanism by which decorin can cause growth suppression.

The finding that EGF receptor is phosphorylated in A431 cells in response to exogenous decorin or its protein core is the first observation linking a secreted proteoglycan to a growth factor receptor and a protracted activation of the MAP kinase cascade. It is well established that not only growth factors, but also divalent cations and cationic polypeptides can increase tyrosine kinase activity of the EGF receptor and cause aggregation of its intracytoplasmic domain (Mohammadi, M. et al. 1993. *Biochemistry* 32:8742–8748). A three-dimensional model of decorin predicts an arch-shaped molecule with ample surface suitable for specific interactions with proteins such as collagen triple helix and cell surface receptors. Because the activation of EGF receptor-MAP kinase pathway occurred within 5 minutes, it is unlikely that decorin interacted with any other molecules, i.e., growth factors synthesized by the cells that could indirectly mediate these effects.

While modulation of the EGF receptor kinase activity and substrate specificity by antibodies to extracellular domains of the receptors (Defize, L. H. K. et al. 1986. *EMBO J.* 5:1187–1192) or by activation of other receptor pathways (Daub, H. et al. 1996. *Nature* 379:557–560) have been shown previously, the experiments described here are the first demonstration of a direct signaling effect of an extracellular matrix proteoglycan. The ability of micromolar concentrations of tyrphostin AG1478, which is highly specific for the EGF receptor, to block the tyrosine phosphorylation and downstream MAP kinase activation induced by decorin implicates direct activation of the EGF receptor tyrosine kinase itself. Indeed, the observation of partial, but significant, inhibition of radiolabeled decorin binding to the A431 cells by exogenous EGF is consistent with a direct interaction. Moreover, the data clearly showed that the growth inhibitory activity of decorin and Δdecorin are significantly blocked by the tyrphostin AG1478. Therefore, the activity of the EGF receptor is required for the growth-suppressive effects of decorin.

The results show that decorin protein core is responsible for a rapid phosphorylation of the EGFR, which leads to a specific activation of the MAP kinase signal pathway and finally to induction of endogenous p21. A specific protein/protein interaction occurs between decorin protein core and the EGFR. Decorin is capable of inducing dimerization of the EGFR in live cells, a physiologic phenomenon previously shown to be a prelude to receptor activation. The specific binding occurs when decorin is immobilized on nitrocellulose membranes or when decorin is free in physiologic salt solution. In a cell-free system, decorin induces autophosphorylation of purified EGFR by activating the receptor tyrosine kinase and can also act as a substrate for the EGFR kinase itself, although it is unlikely to be a substrate in vivo since decorin is an extracellular molecule. Moreover, the data show that decorin is capable of inducing EGFR tyrosine kinase and that both the binding and activation requires intact (properly folded) protein moiety. Taken together, the results demonstrate that the effects of decorin on the EGFR activity are likely mediated in a direct way by this proteoglycan rather than by a transducing mechanism of receptor activation.

As decorin is highly expressed by the host connective tissue stroma surrounding growing neoplasms, it is believed that decorin represents an important defense mechanism designed to counterbalance the invasive nature of cancer cells. Further, it is believed that decorin has a dual function in vivo. First, decorin acts as a key regulator of matrix assembly and cellular growth. By interacting with fibrillar collagens and other molecules involved in inflammation and angiogenesis, decorin modulates matrix assembly thereby influencing the microenvironment of the tumor stroma.

Second, by directly interacting with tumor cell receptors, such as EGF, decorin influences the outcome of abnormal cell proliferation.

Absence of Decorin Favors Tumor Growth in a Genetic Background Where Tumorigenesis is Favored Just as decorin suppresses the growth of tumor cells, its absence favors cancer growth and invasion. This is demonstrated by resort to a genetic background in which tumorigenesis is favored. As shown in the following study, the combination of p53 and decorin deficiency predisposes animals to an accelerated mortality due to enhanced tumorigenesis.

Mice lacking p53 are viable and fertile, but exhibit an increased rate of tumor development and are also prone to genome instability (Donehower, (1996) Semin. Cancer Biol. 7:269–278). In contrast, animals lacking the decorin (Dcn) gene show no overt tumor formation but exhibit a skin fragility phenotype due to the abnormal lateral fusion of collagen fibers (Danielson et al., (1997) J. Cell Biol. 136: 729–743).

Figure 4:
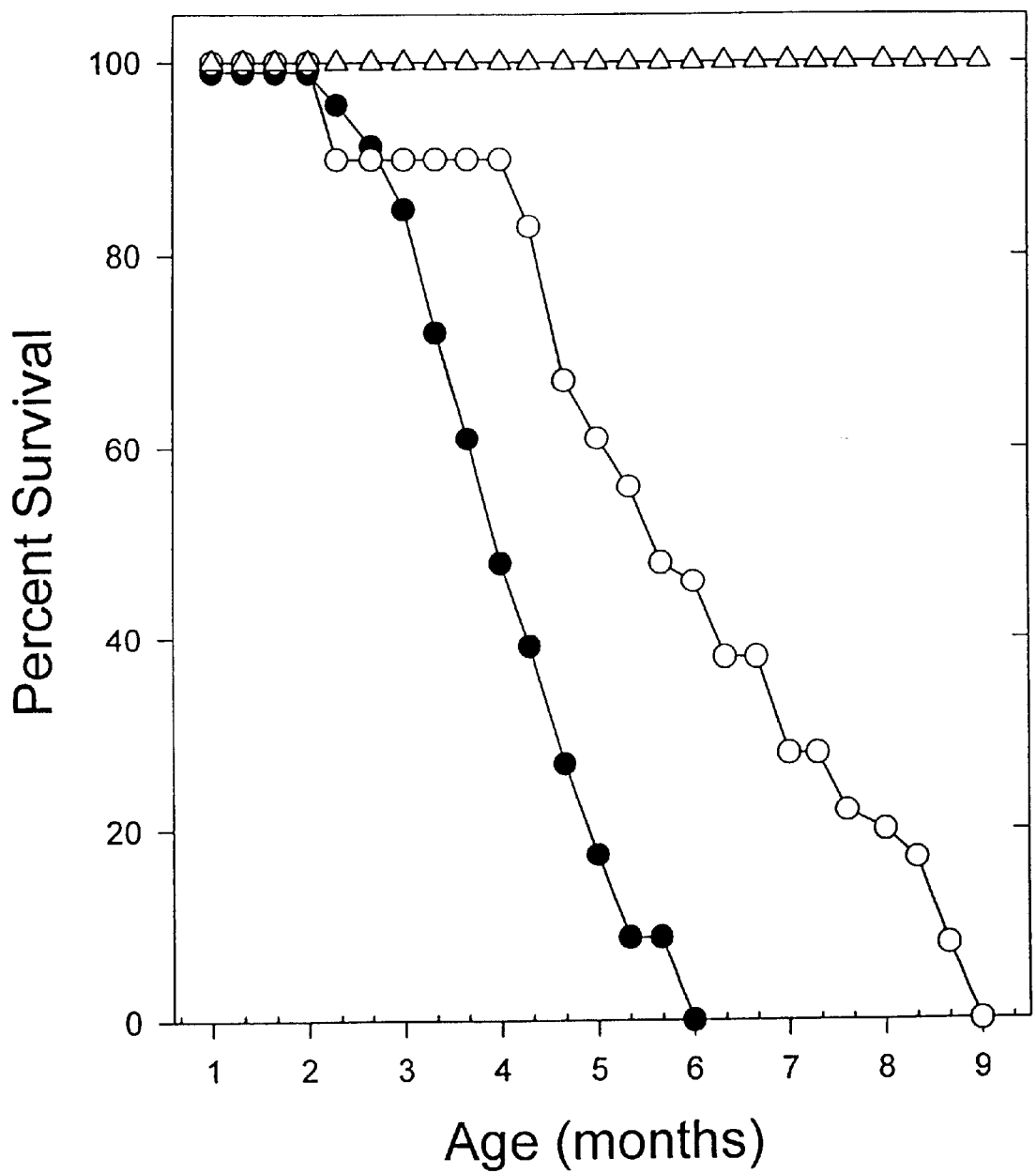
FIG. 4 is a survival curve of mice harboring germline mutations in the tumor suppressor gene p53 and/or decorin (Dcn). The graph summarizes the survival of $p53^{-/-}Dcn^{-/-}$ (n=58; -●-) relative to $p53^{-/-}Dcn^{+/-}$ (n=28; -○-) and $p53^{+/+}Dcn^{-/-}$ (n=68; -▲-). The mean survival age ($T_{50}$) was ~4 and ~6 months for the $p53^{-/-}Dcn^{-/-}$ and $p53^{-/-}Dcn^{+/-}$ genotype, respectively.

Mice homozygous for p53 mutation (Donehower et al., (1992) Nature 356: 215–221), purchased from Taconic (Germantown, N.Y.), were mated with animals homozygous for Dcn mutation (Danielson et al., supra) to generate a series of animals heterozygous for both mutations ($p53^{+/-}$ $Dcn^{+/-}$). The survival rate, tumor formation and histopathological spectrum was investigated in three groups of animals: $p53^{+/+}Dcn^{-/-}$ (n=68), $p53^{-/-}Dcn^{-/-}$ (n=58), and $p53^{-/-}Dcn^{+/-}$ (n=28). The genotype of the animals was determined by PCR analysis using specific primers for p53 and decorin genes and their targeted alleles, respectively. The animals were of mixed genetic background with an average 50% C57 BL/6, 25% 129/Sv and 25% Bl/Swiss. The animals carrying a wild type p53 and a null decorin gene did not develop any tumor for the nine months period of observation (FIG. 4). No preferential tumor development was observed in the $p53^{+/+}Dcn^{-/-}$ animals after nearly two years of observation. Thus, lack of decorin expression alone does not predispose to tumor formation. In contrast, by ~4 months of age, ~50% of the double knockout animals died or required to be sacrificed due to ill health (FIG. 4). By 5 months of age, ~90% of the double knockout succumbed to tumor-growth. No difference between male and female occurrence was noted. The $p53^{-/-}Dcn^{+/-}$ animals survived longer with 50% mean survival rate of ~6 months, similar to that observed in $p53^{-/-}$ animals studied in literature reports. The data indicate that the combination of p53 and decorin deficiency predisposes the animals to an accelerated mortality due to enhanced tumorigenesis. In addition, the presence of a single decorin allele is sufficient to maintain a survival rate similar to that obtained when both wild type decorin alleles are present in the context of a p53 null genetic background.

In contrast to the broad spectrum of tumors generally observed in $p53^{-/-}$ animals, animals carrying both p53 and decorin null alleles showed a remarkable homogeneity in tumor spectrum and exhibited essentially no multiple tumors. Over 95% of the animals developed lymphomas in the thymic region and thus involving primarily the anterior mediastinum. Often the tumors encased the heart, pericardium and lungs and extended into the soft tissues of the neck and chest wall. Because of the massive mediastinal involvement, the mice died as a direct consequence of pericardial compression or respiratory distress. The spleen was rarely affected, possibly due to the rapid appearance of the thymic lymphomas and the relatively shorter survival rate. In only one animal, a high grade hemangiosarcoma was identified in the submandibular region. In a few (~5%) animals, no neoplasm was grossly identified; however histological evaluation showed marked enlargement of the thymus end foci of atypical lymphocytes often infiltrating the mediastinal soft tissues with signs of early invading malignant lymphomas harboring a similar phenotype. The overall tumor spectrum in the $p53^{-/-}Dcn^{+/-}$ animals was essentially identical to that observed in the double knockout animals.

Histopathological examination of the tumors revealed high grade lymphomas with a starry sky appearance. The tumor cells infiltrated the soft tissues of mediastinum, the salivary glands, the periaortic spaces, the pericardium, and the bronchial wall. The microscopic features of these lymphomas were identical in the $p53^{-/-}Dcn^{+/-}$ animals. Primary cultures of three independent thymic lymphomas reveled that the vast majority of the neoplastic cells reacted with antibodies against murine CD4 and CD8, indicating that they arose from the transformation of immature thymocytes (Jacks et al., (1994) Curr. Biol. 4:1–7).

These data demonstrate that the lack of decorin in an otherwise wild-type background is not sufficient by itself to induce tumorigenesis. However, the lack of decorin in a p53 null background accelerates the appearance of tumors, especially T cell-derived lymphomas. The absence of decorin in a p53 deficient genetic background accelerates lymphoma tumorigenesis. The absence of decorin and p53 allows a rapid appearance of the most common tumor in $p53^{-/-}$ animals. The shortened latency of lymphoma tumorigenesis is directly linked to the absence of decorin rather than to a modifier gene associated with a specific genetic background.

Decorin Causes Tumor Cell Growth Suppression in Tumors Arising from p53 Mutations The growth of cancerous cells is significantly inhibited when ectopic expression of decorin was induced, or when exogenous decorin is introduced into cell culture. In particular, results demonstrate that decorin plays a role in restraining lymphomas, particularly lymphomas characterized by p53 mutations.

To investigate the role of decorin in lymphoma tumorigenesis, several clones from freshly minced thymic lymphomas carrying both p53 and decorin null alleles. One clone (designated PD100) was cultured over a confluent monolayer of mouse embryonic fibroblasts (MEF) derived from either wild type or $Dcn^{-/-}$ animals. Cell division of MEFs was arrested by mitomycin C. Thus the only difference between the two sets of feeder layers was the synthesis and release of decorin proteoglycan in the medium (as shown by Western immunoblotting using an antibody directed against the N-terminus of mouse decorin). PD100 lymphoma cells grew faster in the absence of decorin and after 6days of continuous culture there were ~4 times more tumor cells than control (FIG. 4). These experiments were repeated twice with similar results. Cell cycle analysis at each day of co-culture using fluorescence activated cell sorting revealed no cell death or significant block in $G_1$.

Because the only difference between the two fibroblast feeder layers was the presence of secreted decorin, it appears that absence of decorin is permissive for growth of thymic lymphoma cells.

It appears that decorin causes growth retardation in unattached lymphoma cells without causing a block of cell cycle progression, but rather a slowing down of the cell cycle. It is possible that in vivo the reduced rate of mitosis may attenuate or delay the rate of mutations in a p53-deficient genetic background The following nonlimiting examples are provided to further illustrate the present invention.

EXAMPLES

Example 1

Transfection of Cells

The codon of the decorin cDNA encoding the amino acid Ser[7] of the mature protein core was mutated into GCT (Ala) (Mann, D. M. et al. 1990. *J. Biol. Chem.* 265:5317–5323). The Ser-7 holds the glycosaminoglycan sugar chain in the decorin molecule, and it has been shown previously that this mutagenized decorin is secreted as the core protein with no detectable glycosaminoglycan side chain (Mann, D. M. et al. 1990. *J. Biol. Chem.* 265:5317–5323). The mutated decorin cDNA was digested with EcoRI and fused to the 3' end of the human cytomegalovirus (CMV) early gene promoter/enhancer in a mammalian expression vector pcDNA3 (Invitrogen Corporation). The orientation of the insert was verified by restriction endonuclease digestion and DNA sequencing. The full length decorin vector cloned into pcDNA3 is the same as described previously (Santra, M. et al. 1995. *Proc. Natl. Acad.Sci. USA* 92:7016–7020) and results in two transcripts of approximately 1.6 and 1.9 kb, respectively. The Δdecorin contained an additional 200 bp of 3' untranslated region and thus results in two transcripts of approximately 1.6 and 2.1 kb, respectively (Mann, D. M. et al. 1990. *J. Biol. Chem.* 265:5317–5323). Different tumor cell lines (human Saos-2 osteosarcoma, HeLa epidermal carcinoma, HT-1080 fibrosarcoma, HL-60 promyelocytic leukemia cells, and murine M2 melanoma cells) were stably transfected by the calcium phosphate procedure (Santra, M. et al. 1995. *Proc. Natl. Acad. Sci. USA* 92:7016–7020). Briefly, approximately $10^6$ cells were transfected with 20 μg of purified DNA and incubated at 37 C in a humidified incubator for 12–16 hours. After 48 hours of incubation in nonselective medium to allow expression of the transferred genes to occur, the cells were trypsinized and replated at a 1:10 dilution. Within 12–16 hours, G418 (800 μg/ml) was added to the medium with fresh addition of the drug every 4–5 days. Colonies were first detected after 14 days in the selective medium and 7–14 days later, independent colonies were trypsinized in cloning cylinders and transferred to microtiter wells. After 30 days exposure to 800 μg/ml G418, the cells were cultured routinely with G418 (300 μg/ml).

Example 2

Northern and Western Blot Analyses and Cell Proliferation Assays

Total RNA was extracted from the different cells of the colonies of Example 1 using TRI-Reagent™ (Molecular Research Center, Inc.). Total RNA (20 μg per lane) was electrophoresed in formaldehyde/1% agarose gel, transferred to nitrocellulose membranes and hybridized with $^{32}$P-multiprime-labeled (Stratagene Inc.) decorin cDNA (Krusius, T. and E. Ruoslahti. 1986. *Proc. Natl. Acad. Sci. USA* 83:7683–7687) or p21$^{WAF1/CIP1}$ cDNA (El-Deiry, W. S. et al. 1994. *Cancer Res.* 54:1169–1174). Quantity of RNA was normalized on glyceraldehyde-3-phosphate dehydrogenase (GAPDH) mRNA level (Scholzen, T. et al. 1994. *J. Biol. Chem.* 269:28270–28281). For immunoblotting, media conditioned by the various cells for 24 hours in 0.1% serum was precipitated with 5 volumes of ethanol containing 1.3% (wt/vol) potassium acetate at −20° C. overnight and centrifuged at 10,000×g for 5 minutes. Pellets were dried and dissolved in SDS sample buffer, separated in 7.5% Na-dodecylsulfate polyacrylamide gel electrophoresis (SDS-PAGE), transferred onto nitrocellulose membranes and blocked with 5% dried milk for 18 hours. Immunodetection was performed using rabbit polyclonal antipeptide antibodies to decorin (Krusius, T. and E. Ruoslahti. 1986. *Proc. Natl. Acad. Sci. USA* 83:7683–7687), mouse monoclonal 6B6 antibodies directed toward p21. After 3 hours, the filters were rinsed several times with PBS and incubated with 1:5,000 dilution of horseradish peroxidase-conjugated anti-rabbit antibodies for 2 hours. Bound protein was detected with the enhanced chemiluminescence kit (Amersham). The CellTiter 96™ Aqueous Non-Radioactive Cell Proliferation Assay (Promega Corporation) was used to determine the number of viable cells in a proliferative phase (Santra, M. et al. 1995. *Proc. Natl. Acad. Sci USA* 92:7016–7020).

Figure 2A:
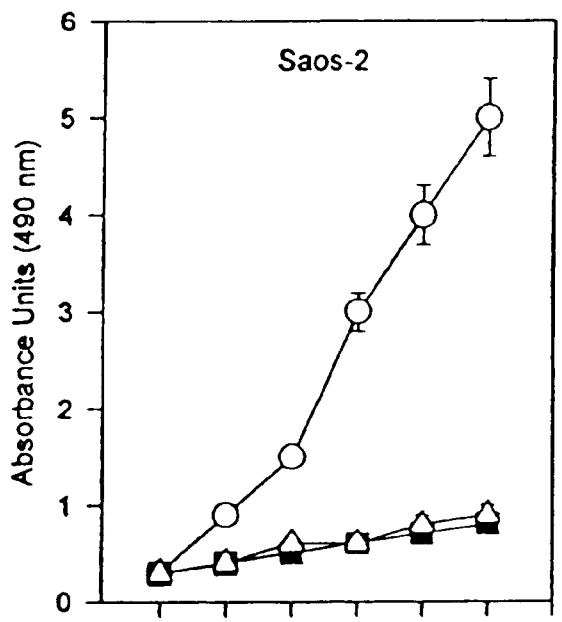
FIGS. 2A–2D illustrate the ectopic expression of decorin (-■-) or its protein core (Δdecorin, -▲-) in human Saos-2 osteosarcoma, HeLa epidermal carcinoma, HT-1080 fibrosarcoma, and murine M2 melanoma cell lines. The number of proliferating cells was established using a non-radioactive tetrazolium/formazan assay using wild-type cells (-○-), or cells synthesizing either the fully glycoslyated decorin (-■-) or Δdecorin lacking the glycosaminoglycan side chain (-▲-). The values are the mean ±SD of three independent experiments (n=5/time point).
Figure 2B:
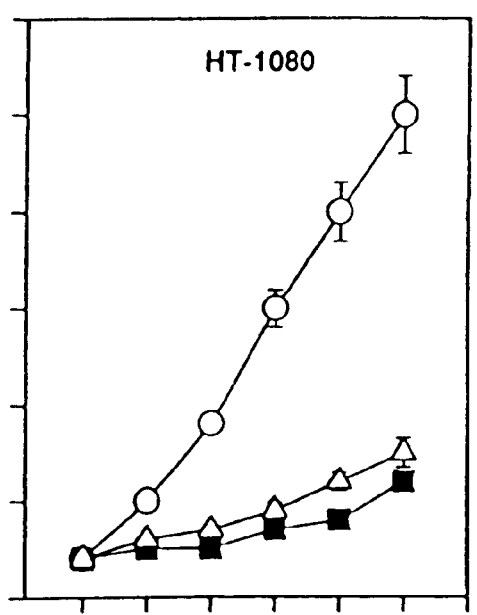
Figure 2C:
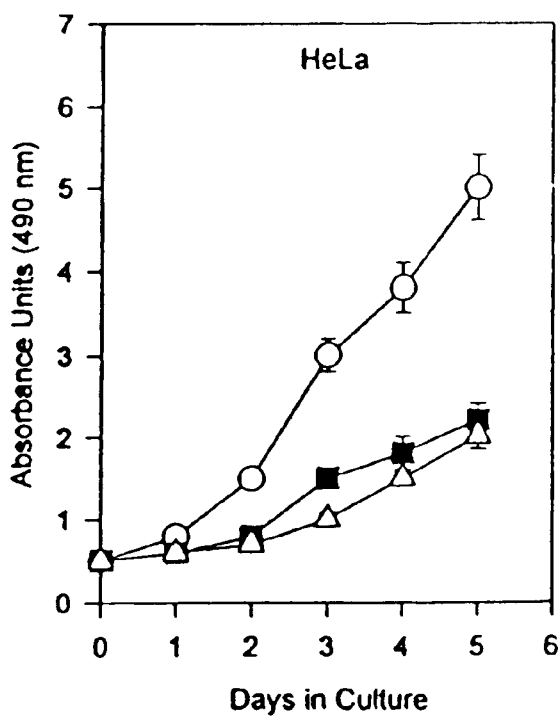
Figure 2D:
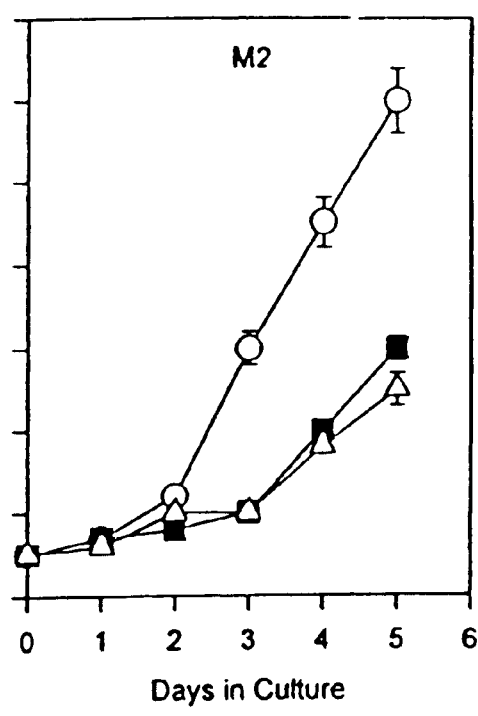

A number of clones expressing various levels of the two transcripts of decorin or Δdecorin were observed (FIG. 1A), with the greatest transfection efficiency in Saos-2 cells. Immunoblofting analysis using antidecorin antibodies and media conditioned for 24 hours by various stably-transfected clones expressing either decorin or Δdecorin showed the expected fully-glycosylated proteoglycan or protein core as ~100 or 42 kD, respectively (FIG. 1B). These experiments were repeated several times with similar results. When the growth kinetics of representative decorin-expressing clones were assessed it was evident that the synthesis of decorin or Δdecorin was sufficient to retard the growth of all the tumor cell lines (FIGS. 2A–2D) with the most profound inhibition occurring in the osteosarcoma Saos-2 cells (FIG. 2A). A marked repression of cell growth comparable to the HT-1080 cells, was also obtained with the HL-60 promyelocytic cells (not shown). As a further negative control for nonspecific effects on cell proliferation, stable transfection of domain III of human perlecan (Iozzo et al. 1996. *FASEB J.* 10:598–614) driven by the same CMV promoter and found no appreciable changes in the growth of HT-1080 cells (not shown).

The similarity of the effects between the cells synthesizing the protein core alone and those synthesizing the fully glycosylated proteoglycan indicated that the growth-suppressive propertied of decorin do not depend on the GAG chains. Furthermore, because the HL-60 cells harbor a homozygous deletion of p53 (Danova et al. *Leuk. Res.* 14:417–422) while the Saos-2 osteosarcoma are essentially defective in the retinoblastoma gene (Shew et al. 1989 *Oncogene Res.* 4:205–214), these results indicated that these two important regulators of the cell cycle are not required for the effects of decorin on tumor cell growth.

Example 3

Exogenous Decorin Inhibition of Transformed Cell Lines

Figure 3:
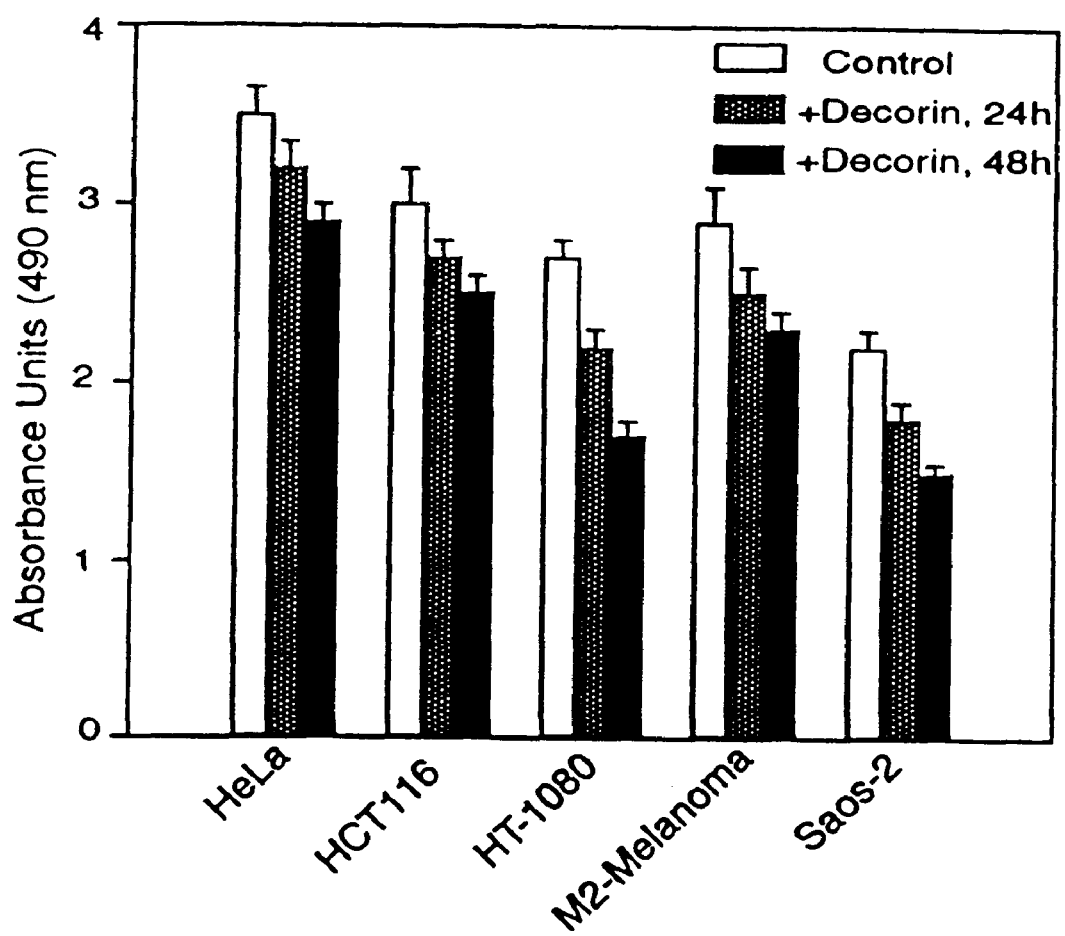
FIG. 3 shows a representative cell proliferation assay (mean ±SD, n=5) of cells (HeLa, HCT116 colon carcinoma, HT-1080, M2 and Saos-2) incubated with either DME alone (Control) or with 100 μg/ml decorin for 24 or 48 hours.

Human recombinant decorin was purified from media conditioned by Chinese hamster ovary cells stably transfected with a decorin expressing vector, as described by Santra et al. 1997. *J. Clin. Invest.* 100:149–157. This highly purified human recombinant decorin, essentially free of contaminating proteins, was tested for biological activity by culturing cell lines (Saos-2 osteosarcoma, HeLa epidermal carcinoma, HT-1080 fibrosarcoma, HCT-116 colon carcinoma, and murine M2 melanoma cells) in the absence or presence of decorin (100 μg/ml; ~1 μM) for 24 and 48 hours respectively. At the end of the incubation, the cell number was measured by nonradioactive calorimetric assay (The CellTiter 96™ Aqueous Non-Radioactive Cell Proliferation Assay, Promega Corporation). In all cases, there was a time-dependent inhibition of growth (FIG. 3), thus corroborating the effects found in the stably expressing colones detailed above.

Example 4

Exogenous Decorin Inhibition of Lymphoma Cell Growth

Figure 5:
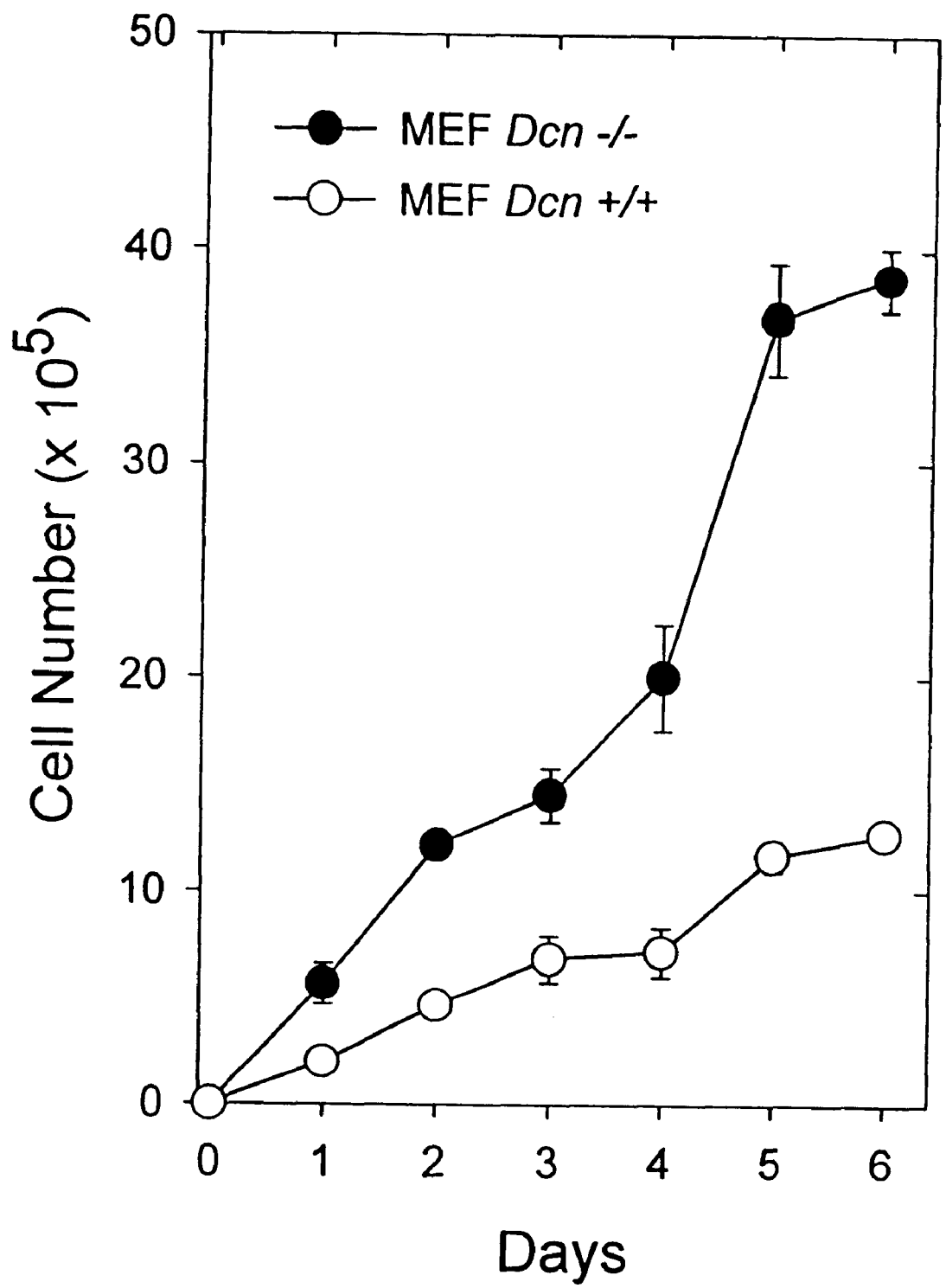
FIG. 5 shows the growth of PD100 thymic lymphoma cells in the presence or absence of a feeder layer composed by mitomycin-arrested mouse embryonic fibroblasts (MEF). The genotype is $Dcn^{-/-}$ (-●-) and $Dcn^{+/+}$ (-○-).
Figure 6A:
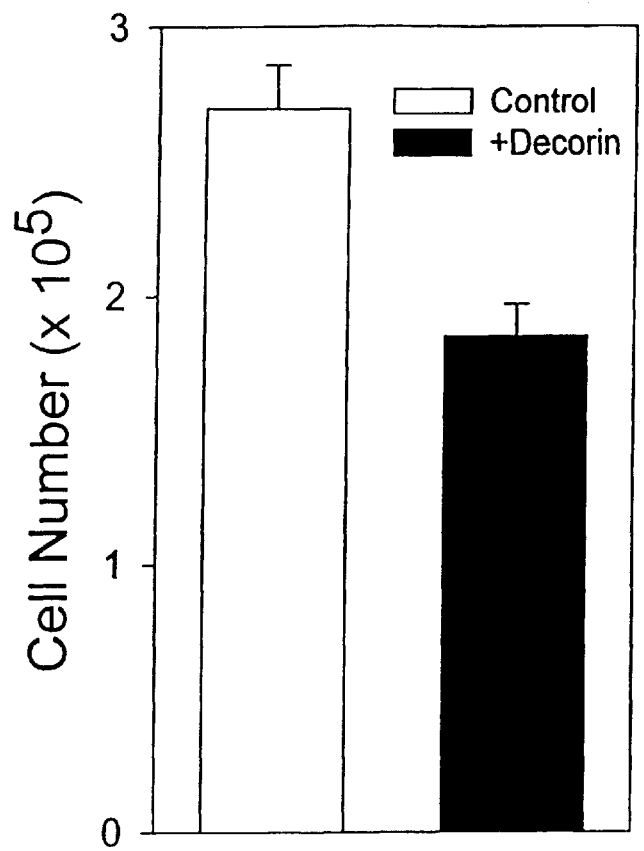
FIGS. 6A and 6B show the growth of PD100 thymic lymphoma cells cultured in the absence or presence of recombinant human decorin (FIG. 6A) or its protein core (FIG. 6B) (1 μM each). Cells were counted after 60 hrs of culture in 5% FBS. The values represent the mean of quadruplicate determinations ±S.E.M.
Figure 6B:
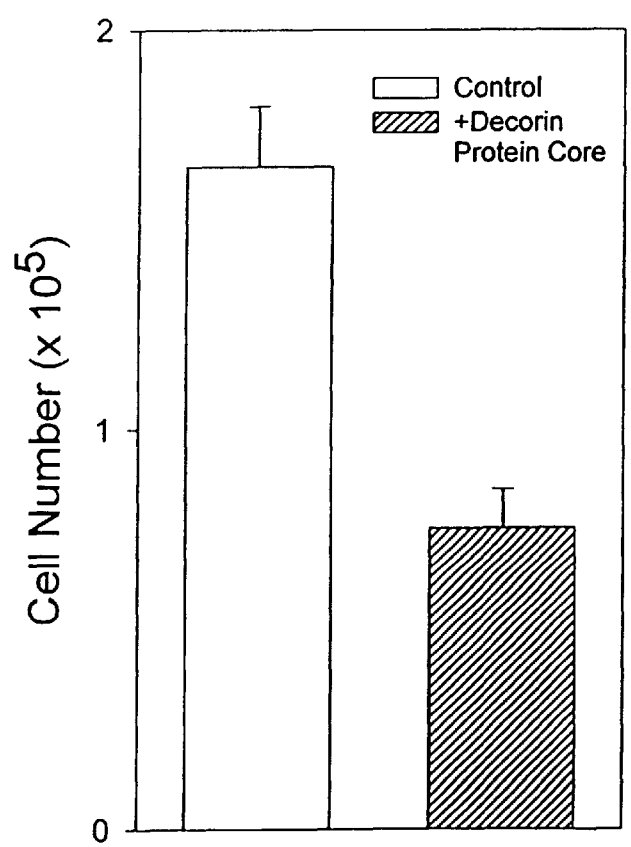

To further investigate these effects, PD100 lymphoma cells were cultured in the presence of 1 μM recombinant human decorin or its protein core. The results showed a significant inhibition of growth (FIG. 5A) and the protein core exhibited a greater cytostatic effect than the proteogylcan (FIG. 5B). These data thus demonstrate that the inhibitory activity resides in the protein moiety rather than the dermatan sulfate chains, and further indicate that these cytostatic properties of decorin transcend species since human decorin can suppress the growth of murine thymic lymphoma cells.

Example 5

Reduction of Lymphoma Colony Formation by Ectopic Decorin Expression

Figure 7:
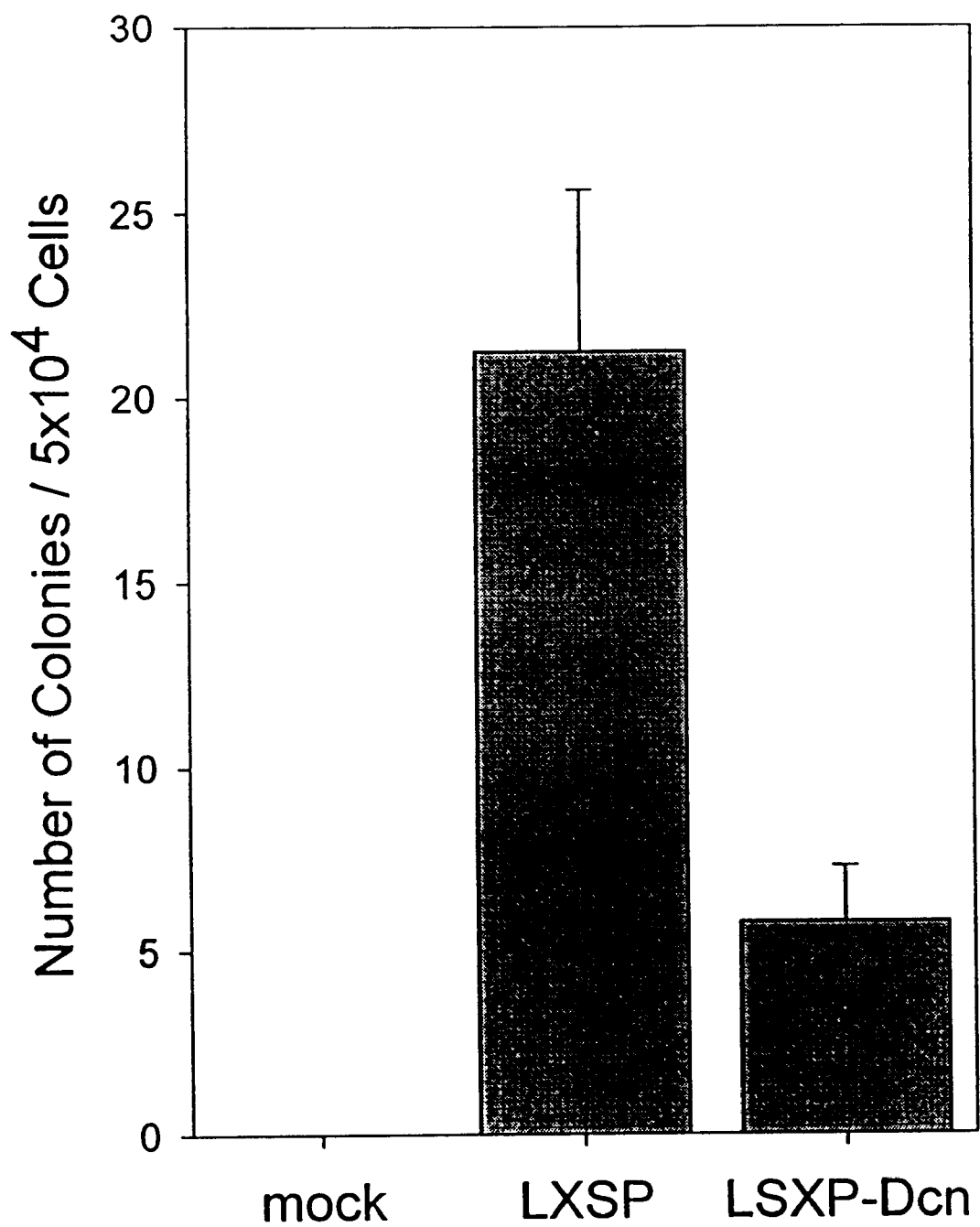
FIG. 7 shows the Inhibition of PD100 colony formation by ectopic decorin expression. Colonies from $5 \times 10^4$ freshly infected PD100 thymic lymphoma cells were grown in methyl cellulose in the presence of puromycin (2 μg/ml) and scored 12 days later. Lane 1: non infected cells; lane 2: cells infected with the empty vector LXSP; lane 3: cells infected with the retrovirus carrying the full-length mouse decorin cDNA. Error bars indicate ±S.D. of the mean of three independent experiments performed in duplicate.

The full-length mouse decorin cDNA was subcloned into the EcoRI restriction site of LXSP retroviral vector (a kind gift of Dr. A. Sacchi, Regina Elena Cancer Institute, Rome) which carries the puromycin resistance gene. T-cell lymphoma cells (PD100) obtained from the $p53^{-/-}Dcn^{-/-}$ double knockout mice were kept in culture in IMDM supplemented with 10% FBS. Infection of $2.5 \times 10^6$ PD100 cells with the retrovirus carrying the full length decorin (LXSP-Decorin) or with the empty virus LXSP, were carried out as described (Sevignani et al., (1998) *J. Clin. Invest.* 101: 1572–1580). Three days post-infection, $5 \times 10^4$ viable cells were plated in semisolid medium [0.9% methyl-cellulose (Stem Cell Technologies: Methocult H4100) in IMDM with 10% FCS] in the presence of puromycin (2 μg/ml). Colonies (>125 μm) were scored 12 days later. After 12 days of selection in the puromycin, the number of puromycin-resistant colonies arising from the decorin-infected cells was markedly diminished (>75% inhibition) as compared to that of cells infected with the vector alone (FIG. 7). Thus, ectopic expression of decorin reduces colony-forming ability of lymphoma cells.

Example 6

Reversible Off/On System for Control of Decorin Expression During Tumor Formation In Vivo The following protocol is used to demonstrate that de novo expression of decorin in tumor cells prevents their growth and invasive potential in vivo. Tumor cells (colon carcinoma or Lewis lung carcinoma) are genetically engineered so that they may be stably transfected with either decorin or Δdecorin (i.e., decorin protein core). Stable transfectant clones are also generated expressing decorin driven by a doxycycline-inducible transactivator/promoterto evaluate growth properties in vivo. By using the latter approach, decorin expression can be switched on in the subcutaneous tumors of recipient mice by adding doxycycline to the drinking water.

A. Selection of Syngeneic Tumor Cells

Two syngeneic tumor cell lines that could be injected subcutaneously into the $Dcn^{-/-}$ and $Dcn^{+/+}$ animals. Both cell lines derive from C57B1/6 mice.

A colon carcinoma cell line has been isolated from the colon of $p53^{-/-}$ animals and transformed with an activated ki-ras oncogene (Sevignani et al., (1998) *J. Clin. Invest.* 101: 1572–1580). These cells form tumors in immunocompromised as well as in syngeneic (C57B1/6) animals.

A highly-metastatic variant of Lewis lung carcinoma, designated 3LL-met (O'Reilly et al. 1994. *Cell* 79:315–328) generates numerous lung metastasises within 2–3 weeks when injected subcutaneously. After 4 weeks post-injection, 3LL-met subcutaneous tumors produced a median of 10 lung metastasises in mice with progressively growing subcutaneous tumors (Dong et al. 1997. *Cell* 88:801–810). Thus, these cells may be used to demonstrate that de novo expression of decorin would retard the metastatic growth and whether the lack of decorin (in the host animals) would favor metastasis.

B. Stable Transfectant Tumor Cells Expressing Decorin

The generation of colon and lung carcinoma cells constitutively expressing decorin proteoglycan or Δdecorin is carried out as follows. The above colon and lung tumor cells are transfected and cloned essentially as described before (Santra, M. et al. 1995. *Proc. Natl. Acad. Sci. USA* 92:7016–7020 and Santra et al., (1997) *J. Clin. Invest.* 100:149–157). Briefly, the codon (TCT) of the decorin cDNA encoding the amino acid $Ser^7$ of the mature protein core is mutated into GCT (Ala) (Mann et al., *J. Biol. Chem.* 1990. 265:5317–5323). The $Ser^7$ is linked to the single glycosaminoglycan chain in the decorin molecule and it has been previously shown that this mutant decorin (Δdecorin) is secreted as the core protein with no detectable glycosaminoglycan side chain. The mutated mouse decorin cDNA is digested with EcoRI and fused to the 3' end of the human CMV early gene promoter/enhancer in a mammalian expression vector pcDNA3 (Invitrogen). The orientation of the insert is verified by restriction endonuclease digestion and DNA sequencing.

The colon carcinoma and lung tumor cell lines are stably transfected by the calcium phosphate procedure (Santra, M. et al. 1995. *Proc. Natl. Acad. Sci. USA* 92:7016–7020). G418 resistant colonies are isolated in cloning cylinders and the cells are detached with trypsin and transferred to microtiter wells. After 30-day selection in 600 μg/ml G418 (active drug concentration), the clones are routinely cultured with G418 (300 μg/ml).

C. Creation of a Reversible Off/On System for the Tight Control of Decorin Gene Expression During Tumor Formation In Vivo Conditional regulation of decorin gene expression, for demonstrating the course of in vivo tumor progression in the presence or absence of decorin expression, is obtained as follows.

The tetracycline (Tet)-regulated eukaryotic expression vector (Gossen and Bujard. 1992. *Proc. Natl.Acad. Sci. USA* 89:5547–5551; Kistner et a. 1996. *Proc. Natl. Acad. Sci. USA* 93:10933–10938) is utilized to obtain conditional regulation of decorin gene expression. A Tet-controlled hybrid transactivator (tTa), a fusion protein containing the repressor of the *E. Coli*-derived Tet resistance operon and the activating domain of herpes simplex virus protein (VP16) encoded by a regulator plasmid, is expressed under the control of a CMV promoter/enhancer. The expressed tTa induces target gene transcription via binding to the Tet operator sequences located upstream of a minimal promoter of a co-introduced response plasmid (Gossen and Bujard, supra). Tet inhibits this tTa-dependenttransactivation via its affinity to tTa. In doubly transfected cells, thus, the activity of a given transgene, e.g., decorin, can be controlled by exogenous tetracycline.

Accordingly, stably transfected clones derived from the mouse colon carcinoma and 3LL-met are generated expressing decorin controlled by a doxycycline-inducible promoter. The clones are generated using the Clontech's Tet-On™ system, according to the manufacturer's instructions. This system provides a high level of inducible expression (up to 1,000 fold induction), quantitative regulation of gene expression, and minimal pleiotropic and non specific effects. The fusion protein of VP16 is a mutant tet repressor differing from the wild type by 4 amino acids (Kistner et al, supra). Thus, activation of gene transcription occurs in the presence of tetracycline and is enhanced in the presence of its derivative doxycycline (Gossen et al. 1995. *Science* 268:1766–1769).

Cells are transfected with the regulator plasmid and selected with G418. Highly-responsive clones and clones with minimal base-line activity are selected by transient transfection with a luciferase construct driven by a promoter containing 7 repetitive TRE (tet-responsive elements) according to the manufacturer's instructions (Clontech). After a suitable responsive clone is identified, it is co-transfected with the pTRE cloning vector [which contains the TRE upstream of a minimal CMV promoter/ decorin cDNA] and an hygromycin cassette as the second selection marker (Gossen et al. 1995. *Science* 268:1766–1769). Hygromycin-resistant clones are isolated and tested for growth in vitro and in vivo as described below. For in vivo testing, the clones are implanted into $Dcn^{-/-}$ mice, for example.

Example 7

Assay of In Vitro Tumorigenicity of Transfectant clones Conditionally Expressing Decorin Anchorage-independent growth of transformed cells correlates with their in vivo tumorigenicity (Shin et al., 1975. *Cell* 72:4435–4439; Cox and Der, 1994. *Methods Enzymol.* 238:277–294). Therefore, the morphologic and growth kinetics changes in the stably transfected clones, i.e., changes in contact inhibition, formation of cellular foci with different properties and growth potential in semi-solid media are evaluated in the presence or absence of decorin expression. Briefly, agarose suspensions are prepared as described before (Danielson et al. 1980. *Cancer Res.* 40:1812–1819). A thin layer of 0.5% agarose in DMEM, supplemented with 10% fetal bovine serum, is added to a 25 cm²—flask and allowed to solidify. A suspension of ~$10^5$ cells will be gently mixed in 0.33% agarose and then layered over the agarose base. The flask is then sealed and colonies are scored at 14 and 21 days by counting aggregates of >100 cells (~100 $\mu$m in diameter) over several randomly chosen 4 mm² areas. For the conditional expression of decorin, the highly-responsive clones are grown in agarose suspension cultures supplemented with 1 $\mu$g/ml doxycycline (Liaudet-Coopman et al., 1997. *Biochem. Biophys. Res. Comm.* 229:930–937). These studies establish the baseline for gross changes in behavior and represent a means of selecting transfected clones to be used in the animal studies described below.

Example 8

Assay of In Vivo Tumorigenicity of Transfectant Clones Conditionally Expressing Decorin Cells (about $10^6$) of transfectant clones conditionally expressing decorin are initially inoculated in the left or right flank of syngeneic mice. The mice are monitored for tumor growth using a caliper every other day. The growth kinetics and the deduced volume of each subcutaneous tumor is estimated based on the volume of an ellipsoid, that is, $4/3\pi(a/2)^2$ (b/2), where a=shorter diameter, and b=larger diameter.

Example 9

In Vivo Decorin Inhibition of Colon Carcinoma Tumor Growth

The colon carcinoma of Example 6A and syngeneic C57BI/6 mice were utilized. This study demonstrates the lack of decorin in the connective tissue of decorin null mice allows expression of a more aggressive malignant phenotype.

Figures 8A, 8B:
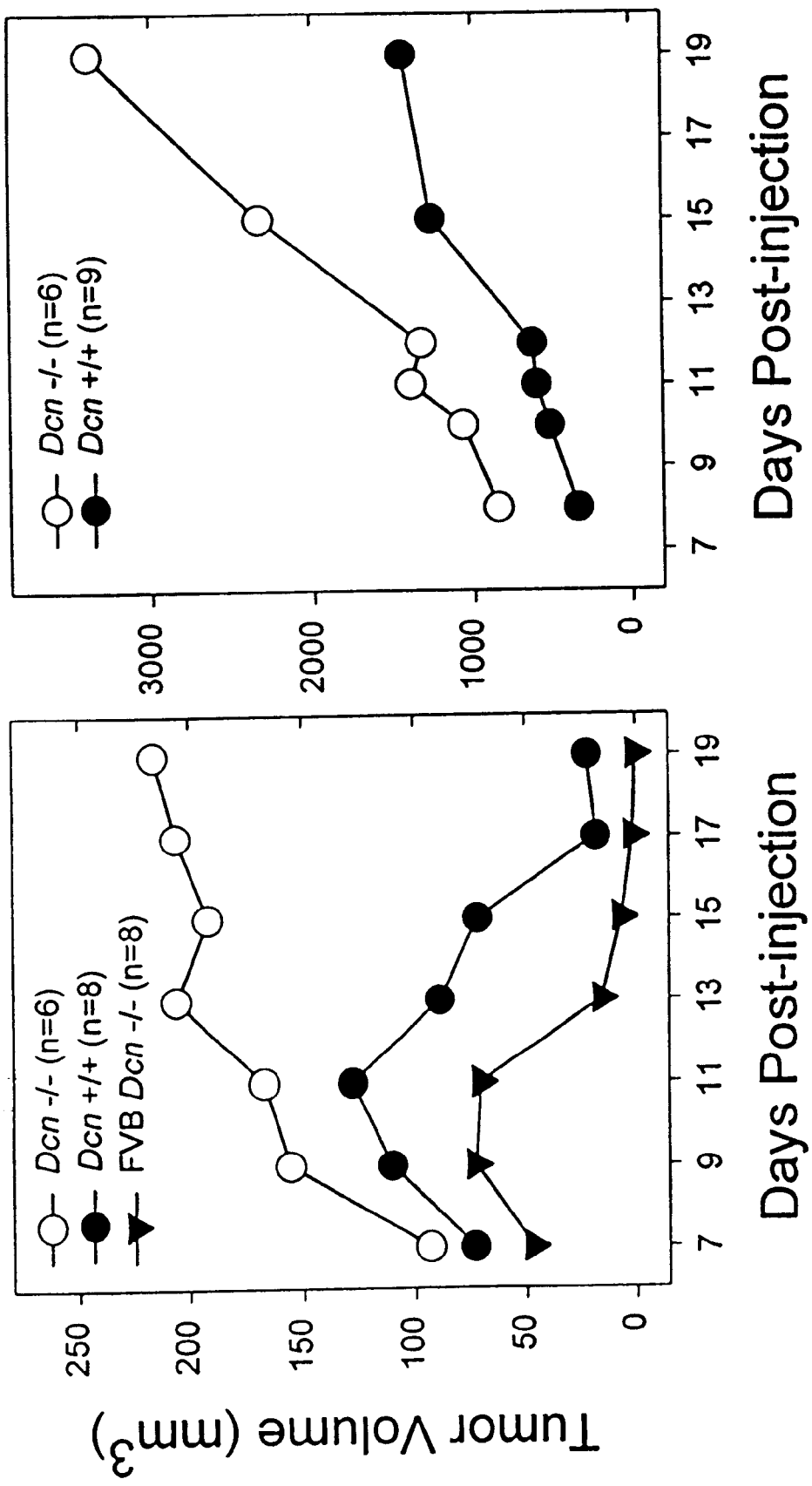
FIGS. 8A and 8B show the growth of ~$0.5 \times 10^6$ (FIG. 8A) and ~$2.5 \times 10^6$ (FIG. 8B) syngeneic colon carcinoma cells injected subcutaneously into the right flank of $Dcn^{+/+}$ and $Dcn^{-/-}$ animals.

Either ~$0.5 \times 10^6$ (FIG. 8A) and ~$2.5 \times 106$ (FIG. 8B) of the colon carcinoma cells were injected subcutaneously into the right flank of $Dcn^{+/+}$ and $Dcn^{-/-}$ animals. Cells were also injected into nonsyngeneic 9 FVB) $Dcn^{-/-}$ mice. Tumor volume was determined as in Example 8. the results appear in FIGS. 8A and 8B: FIG. 8A: (-○-), $Dcn^{-/-}$ (n=6); ( -●-), $Dcn^{+/+}$ (n=6); (-▼-), FVB $Dcn^{-/-}$ (n=6). FIG. 8B: (-○-), $Dcn^{-/-}$ (n=6); (-●-), $Dcn^{+/+}$ (n=9). All values are the average with SD<15% of the mean. At both cell dosages, the volume of the subcutaneous tumors in the $Dcn^{-/-}$ animals was significantly greater throughout the entire course of the experiment. The $Dcn^{+/+}$ animals' tumor size declined after 11 days (FIG. 8A) whereas in the larger inoculum (FIG. 8B) it continued to grow even after 19 days post-injection. When tumor cells were injected into a nonsyngeneic $Dcn^{-/-}$ animal with a FVB background (FIG. 8A), the tumors achieved the smallest dimension and declined at a faster rate. This is likely due to a florid immunological response. Notably, not only the growth rate but also the morphology of the tumors in the $Dcn^{-/-}$ animals was quite different than the wild type animals. In the latter there were solid areas and more differentiated tumor foci with gland-like structures. Moreover, there was a prominent desmoplastic response with broad collagen fibers at the periphery of the tumor, as better shown by trichrome stain, as well as in the central region of the tumor. In contrast, in the $Dcn^{-/-}$ animals there was markedly reduced desmoplastic response and the advancing edges of these subcutaneous tumors were more irregular with infiltrating columns of cancer cells. Interestingly, the desmoplastic reaction around the subcutaneous tumors coincide with deposition of decorin epitopes as detected by immunohistochemistry using an anti-decorin antibody.

Example 10

In Vivo Decorin Inhibition of Lung Carcinoma Tumor Growth

Figure 9:
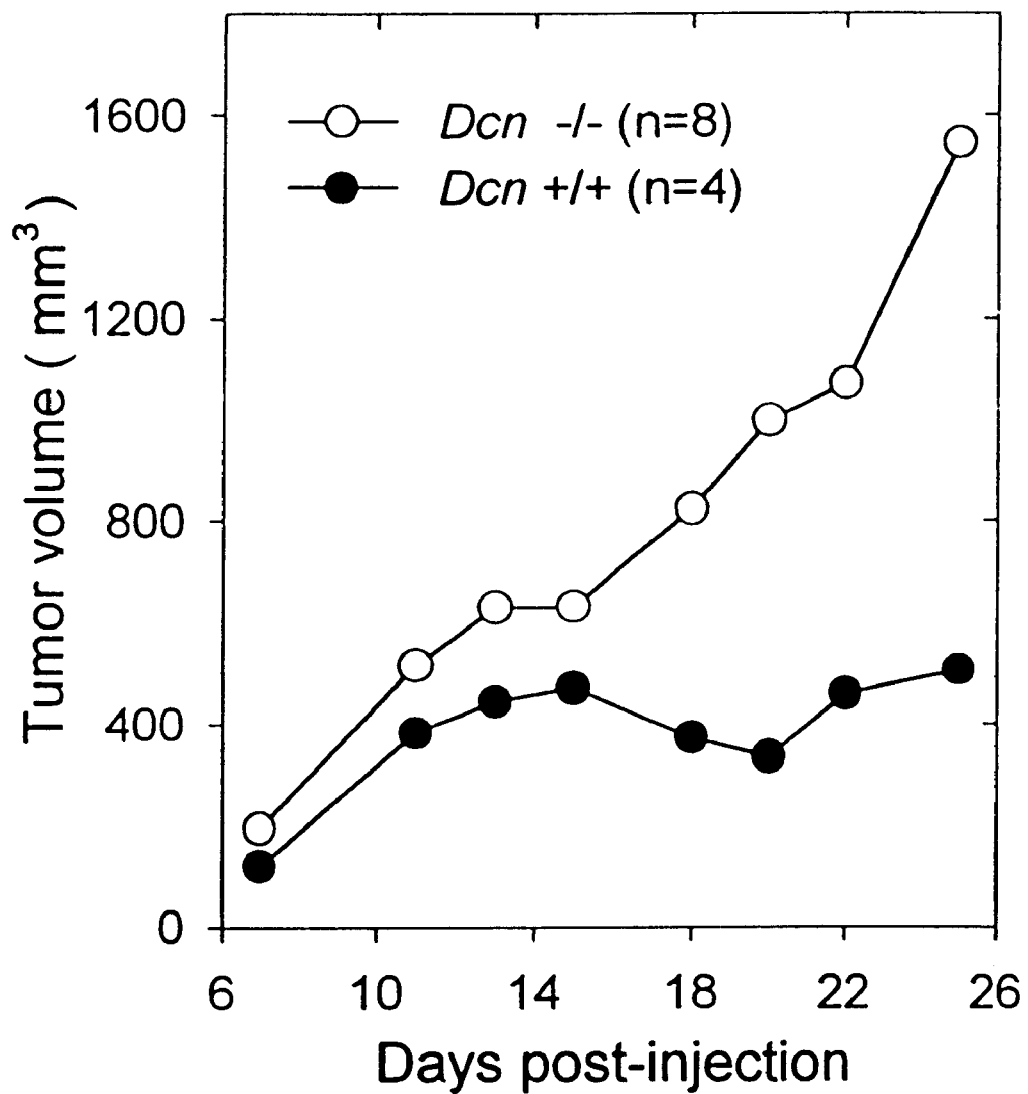
FIG. 9 shows the growth of syngeneic Lewis lung carcinoma cells (low metastatic) in $Dcn^{+/+}$ (-●-, n=4) and $Dcn^{-/-}$ (-○-, n=8) animals. The values are the averages with SD<15% of the mean.

Low-metastatic Lewis lung carcinoma cells were injected into the mid-dorsum of 12 age-matched C57 BI/6 mice (8 $Dcn^{-/-}$, and 4 $Dcn^{+/+}$). The results are shown in FIG. 9. As in the case of colon carcinoma cells, the tumor allografts induced by the Lewis lung carcinoma cells grew faster and achieved larger dimensions in the Dcn null animals. At 25 days post-injection there was a four fold difference between the decorin nullizous and wild-type animals. These results, and the results of the previous example, further demonstrate that the local absence of decorin may be permissive for an aggressive phenotype. Administration of decorin will therefore inhibit an aggressive phenotype.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for suppressing tumor cell growth in an animal comprising local administration of a viral vector encoding a decorin gene product to a tumor site of said animal suffering from a solid tumor or cancer expressing an Epidermal Growth Factor Receptor, so that said tumor cell growth is suppressed in said animal.

2. A method according to claim 1 wherein said viral vector encodes wild-type decorin.

3. A method according to claim 1 wherein said viral vector encodes Δdecorin.

4. A method according to claim 1 wherein said viral vector is a retroviral vector.

5. A method according to claim 1 wherein said viral vector is an adenoviral vector.

6. A method according to claim 1 wherein said viral vector is administered to in a patient.

7. A method according to claim 1 wherein the vector is administered to normal cells of the animal ex vivo to obtain over-expression of the decorin gene product and the, which cells are then returned to the body of the animal in the vicinity of the tumor.

8. A method according to claim 1 wherein said tumor is characterized by a deleterious p53 mutation.

9. A method according to claim 1 wherein the animal is a human being.

10. A method according to claim 9 wherein the tumor is selected from the group consisting of osteosarcoma; fibrosarcoma; colon carcinoma; melanoma; epidermal carcinoma; breast carcinoma; brain carcinoma; lung carcinoma; pancreatic carcinoma; prostate carcinoma; testicular carcinoma; gynecological carcinoma; endometrial carcinoma; head and neck carcinoma; and carcinoma of the oral cavity, throat or stomach.

* * * * *

UNITED STATES PATENT AND TRADEMARK OFFICE
CERTIFICATE OF CORRECTION

PATENT NO. : 6,524,573 B2 Page 1 of 1
APPLICATION NO. : 09/668084
DATED : February 25, 2003
INVENTOR(S) : Renato V. Iozzo It is certified that error appears in the above-identified patent and that said Letters Patent is hereby corrected as shown below:

In the Specification

On Column 1, Lines 12-17, please replace the existing section with the following section:
-- ACKNOWLEDGEMENT OF GOVERNMENT RIGHTS This invention was made with government support under CA039481 and CA047282 awarded by the National Institutes of Health. The government has certain rights in the invention. --

Signed and Sealed this
Twenty-seventh Day of May, 2025

Coke Morgan Stewart
*Acting Director of the United States Patent and Trademark Office*